(12) United States Patent
Inagaki et al.

(10) Patent No.: US 6,309,536 B1
(45) Date of Patent: Oct. 30, 2001

(54) METHOD AND APPARATUS FOR DETECTING A FUNCTIONAL CONDITION ON AN NOX OCCLUSION CATALYST

(75) Inventors: Hirosi Inagaki; Noriaki Kondo; Shigeru Miyata, all of Aichi (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/172,017

(22) Filed: Oct. 14, 1998

(30) Foreign Application Priority Data

| Oct. 14, 1997 | (JP) | ................................................... | 9-280551 |
| Nov. 26, 1997 | (JP) | ................................................... | 9-324777 |
| Nov. 26, 1997 | (JP) | ................................................... | 9-324778 |

(51) Int. Cl.⁷ ........................... G01N 27/407; F01N 3/10
(52) U.S. Cl. ......................... 205/781; 204/425; 204/426; 204/408; 60/277; 60/301
(58) Field of Search ................................... 204/424–429, 204/408; 205/781, 784, 784.5, 785; 60/277, 301

(56) References Cited

U.S. PATENT DOCUMENTS

| 4,875,990 | * | 10/1989 | Kodachi et al. ........................ 204/408 |
| 5,239,971 | | 8/1993 | Uchinami ............................... 123/676 |
| 5,644,912 | * | 7/1997 | Kawamura .............................. 60/277 |
| 5,750,888 | * | 5/1998 | Matsumoto et al. ..................... 73/118.1 |
| 5,758,491 | * | 6/1998 | Agustin et al. ......................... 60/274 |
| 5,771,686 | * | 6/1998 | Pischinger et al. ..................... 60/274 |
| 5,772,965 | * | 6/1998 | Kato et al. ............................. 422/98 |
| 5,866,799 | * | 2/1999 | Kato et al. ............................. 73/31.05 |
| 6,012,282 | * | 1/2000 | Kato et al. ............................. 60/274 |
| 6,026,640 | * | 2/2000 | Kato et al. ............................. 60/274 |
| 6,116,082 | * | 9/2000 | Pride ...................................... 73/40 |

FOREIGN PATENT DOCUMENTS

| 0 678 740 A1 | 10/1995 | (EP) . |
| 0 733 787 A | 9/1996 | (EP) . |
| 62-153546 | 7/1987 | (JP) . |
| 9530146 | * 11/1995 | (WO) . |

OTHER PUBLICATIONS

Nobuhide Kato et al., "Thick Film ZrO2 Nox Sensor", Society of Automotive Engineers, Inc., 1996, pp. 137–142. Month n/a.

* cited by examiner

Primary Examiner—Robert J. Warden, Sr.
Assistant Examiner—Kaj K. Olsen
(74) Attorney, Agent, or Firm—Sughrue, Mion, Zinn, Macpeak & Seas, PLLC

(57) ABSTRACT

A method and apparatus for detecting a functional condition of an NOx occlusion catalyst using an NOx sensor. In order to compensate for variations in oxygen concentration of the exhaust gas which would otherwise affect the detected NOx concentration downstream of the NOx occlusion catalyst, a relative value is calculated as the difference between the detected NOx concentration and the value of the detected NOx concentration initially after start of operation control of an internal combustion engine at a lean air-fuel ratio. The occlusion capability of the NOx occlusion catalyst is judged to have deteriorated when an increase in the relative value exceeds a predetermined value. On the other hand, the NOx occlusion catalyst is judged to have suffered an anomaly when the rate of increase in the relative value becomes greater than a predetermined allowable value.

10 Claims, 16 Drawing Sheets

METHOD AND APPARATUS FOR DETECTING A FUNCTIONAL CONDITION ON AN NOx OCCLUSION CATALYST

FIELD OF THE INVENTION

The present invention relates to a method and apparatus for detecting a functional condition of an NOx occlusion catalyst, using an NOx sensor adapted to detect the concentration of NOx emitted from various combustion apparatus, including internal combustion engines.

BACKGROUND OF THE INVENTION

NOx-concentration detecting apparatus for detecting the concentration of NOx (NOx) contained in exhaust gases from internal combustion engines and the like using an NOx sensor are disclosed, for example, in European Patent Application Laid-Open No. 0678740A1 and SAE Paper No. 960334, pp. 137–142, 1996. An NOx sensor used in such a conventional NOx-concentration detecting apparatus is composed of oxygen-ion conductive solid electrolyte layers that define a first measurement space and a second measurement space. The first measurement space communicates with a gas to be measured (hereinafter called "a measurement gas") via a first diffusion-controlling layer, and the second measurement space communicates with the first measurement space via a second diffusion-controlling layer. Furthermore, the solid electrolyte layer of the first measurement space is sandwiched between porous electrodes so as to form a first oxygen-pumping cell and an oxygen-concentration-measuring cell. Also, the solid electrolyte layer of the second measurement space is sandwiched between porous electrodes so as to form a second oxygen-pumping cell.

In the thus-configured NOx-concentration detecting apparatus, current is applied to the first oxygen-pumping cell such that the output voltage from the oxygen-concentration-measuring cell achieves a predetermined value, thereby controlling the concentration of oxygen contained in the first measurement space at a constant level. At the same time, a constant voltage is applied to the second oxygen-pumping cell to thereby pump out oxygen from the second measurement space. At this time, the NOx concentration of a measurement gas can be obtained by measuring the current flowing through the second oxygen-pumping cell.

A measurement gas, e.g., exhaust from an internal combustion engine or the like, contains gas components other than NOx, such as oxygen, carbon monoxide and carbon dioxide. Thus, in the aforementioned NOx-concentration detecting apparatus, first, the first oxygen-pumping cell is activated so as to control the concentration of oxygen contained in the first measurement space to a very low level. Then, in the second measurement space into which the measurement gas controlled to a low oxygen concentration flows, a constant voltage is applied to the second oxygen-pumping cell in a direction such that oxygen is pumped out from the second measurement space. As a result, NOx contained in the measurement gas is decomposed into nitrogen and oxygen by means of the catalyzing function of the porous electrodes of the second oxygen-pumping cell, and the thus-generated oxygen is then pumped out from the second measurement space. Thus, the NOx concentration of the measurement gas can be obtained by measuring the current flowing through the second oxygen-pumping cell with no influence of other gas components contained in the measurement gas.

In an NOx-concentration measuring apparatus of this kind, in order to accurately detect the concentration of NOx by the detecting method described above, the sensor must be heated to a predetermined active temperature (for example, 800° C. or higher) so as to activate the cells. Therefore, a heater for heating the sensor is additionally provided.

In recent years, in order to improve fuel consumption and attain high efficiency for internal combustion engines using gasoline as a fuel, internal combustion engines have been developed that are controlled so as to operate at a lean air-fuel ratio, where the amount of air is large with respect to that of the fuel (lean burn engines, direct injection engines, etc.). Normally, in an internal combustion engine, NOx and unburned components (HC and CO) contained in exhaust gas are made to react with each other using a three-way catalytic converter to reduce NOx to $N_2$, thereby purifying the exhaust gas. In operating at a lean air-fuel ratio, a large amount of oxygen is contained in the exhaust gas. As a result, the oxygen reacts with unburned components, resulting in a failure to remove NOx.

To solve the above problem, a so-called NOx occlusion catalyst is used, which is a three-way catalytic converter containing an NOx storage material for storing NOx contained in exhaust gas in the form of nitrate. However, because of the limited amount of NOx that can be occluded in the NOx occlusion catalyst, the control for refreshing the NOx occlusion catalyst so as to restore its capacity for storing NOx is performed in the following manner. The air-fuel ratio of a mixture fed to an internal combustion engine is temporarily controlled to a rich air-fuel ratio, where the amount of fuel is relatively large, before the amount of stored NOx reaches the above capacity limit. The resulting exhaust gas contains a large amount of unburned components from the internal combustion engine. This causes the unburned components to react with NOx stored in the NOx occlusion catalyst, thereby refreshing the NOx occlusion catalyst so that its capability of storing NOx is restored.

Such a refreshing operation is performed periodically at constant intervals or when the amount of leakage of NOx from the NOx occlusion catalyst exceeds a predetermined level. In the latter case, the amount of NOx leakage is detected using the NOx-concentration measuring apparatus described above, including the NOx sensor installed in an exhaust passage of the internal combustion engine at a location downstream of the NOx occlusion catalyst.

In order to perform accurate control, the NOx sensor used in such an application must at least be able to determine the NOx concentration in units of 100 ppm.

SUMMARY OF THE INVENTION

1. Problems to be Solved by the Invention

In the NOx sensor, when the oxygen concentration in the first measurement space is controlled to zero by controlling the pumping current, NOx components contained in a measurement gas contained in the first measurement space are gas contained in the first measurement space are decomposed. As a result, the NOx concentration cannot be measured using the second oxygen-pumping cell. Normally, therefore, the oxygen concentration in the first measurement space is controlled such that a small amount of oxygen remains within the first measurement space (for example, a low oxygen concentration of about 1000 ppm). Accordingly, a second pumping current flowing through the second oxygen-pumping cell includes an offset due to the influence of the remaining oxygen. FIG. 11 schematically shows the relationship between the oxygen concentration in a measurement gas and the first pumping-current, as well as the relationship between the NOx concentration and the second pumping-current.

FIG. 12 shows the results of measuring offset of the second pumping current when an apparatus is operated while a test gas not containing NOx is used as a measurement gas (measurement with three different sensors).

The line with circles indicates an NOx sensor No. 1, the line with black diamonds indicates an NOx sensor No. 2, and the line with black triangles indicates an NOx sensor No. 3.

As shown in FIG. 12, the amount of offset varies depending on the differences between NOx sensors and also on the air-fuel ratio of the measurement gas. When the air-fuel ratio varies with changes in operating conditions or the like, the offset varies accordingly, by several to tens of ppm. However, in order to accurately perform refreshment control for the NOx occlusion catalyst, the NOx concentration must at least be determined in units of 100 ppm. Thus, a sufficient detection accuracy has not yet been obtained.

Thus, in order to reliably prevent the increase in NOx leakage from the NOx occlusion catalyst beyond a predetermined value, a refreshing operation must be initiated while considerable allowance is given to the NOx occlusion capability of the NOx occlusion catalyst in view of variations in offset. This causes a failure to sufficiently utilize the capability of the NOx occlusion catalyst. This tendency is also observed when the refreshing operation is performed periodically.

When sulfur (S) is present in exhaust gas, the NOx occlusion catalyst stores the sulfur, in the form of sulfate, on an NOx storage material. Since sulfate is less likely to react with unburned components than is nitrate, sulfate cannot be removed by executing the refreshing operation described above. As a result, the NOx occlusion capability deteriorates to an extent corresponding to the amount of accumulated sulfate.

When the NOx occlusion capability deteriorates as above, in the case of periodic refreshment, the cleaning capability with respect to NOx deteriorates. On the other hand, whereas in the case of refreshment based on a detected NOx concentration, refreshment is performed frequently, causing a deterioration in fuel consumption and efficiency of the internal combustion engine.

It is known that, by executing, for example, the above-described refreshment with the NOx occlusion catalyst being held at a higher temperature (hereinafter referred to as catalyst burnout), sulfate can be removed by reacting with unburned components. Thus, conceivably, sulfate can be removed periodically. However, because of a larger burden on the NOx occlusion catalyst as compared with the case of normal refreshment for the removal of nitrate and potential deterioration of the NOx occlusion catalyst, sulfate removal is desirably performed only as needed.

On the other hand, FIG. 16 shows a second pumping current IP2 measured with the NOx sensor located downstream of the NOx occlusion catalyst when the operation control mode of an internal combustion engine is switched from operation control at a theoretical air-fuel ratio to operation control at a lean air-fuel ratio.

As shown in FIGS. 16(*a*) and 16(*b*), immediately after operation control at a theoretical air-fuel ratio is switched to operation control at a lean air-fuel ratio (time t0), the concentration of oxygen contained in exhaust gas varies greatly, and thus the second pumping current varies transiently. In order to wait for variation in the second pumping current to settle, a waiting time Tw is provided. A second pumping current first detected after the elapse of the waiting time Tw is determined to be a reference value IP2s.

In the case of determining the reference value IP2s as above, the following problem is involved. When the occlusion capability of the NOx occlusion catalyst deteriorates significantly due to, for example, exfoliation of a large amount of an NOx occlusion material, the second pumping current IP2 increases abruptly immediately after the operation control mode is switched to lean control, as shown in FIG. 16(*c*). In this case, at time t1 when detection is first carried out after elapse of the waiting time Tw, the second pumping current IP2 has already increased greatly. Thus, if the second pumping current IP2 detected at time t1 is used as the reference value IP2s in calculating a relative value of a subsequently detected second pumping current IP2, the relative value will not exceed the predetermined value Ic, which serves as a reference value in judging a functional deterioration of the NOx occlusion catalyst. As a result, control may be disabled.

Thus, an object of the present invention is to provide a method and apparatus for accurately detecting a functional condition of an NOx occlusion using an NOx sensor.

2. Means for Solving the Problems

The above object of the present invention has been achieved by providing:

(1) A method for detecting a functional condition of an NOx occlusion catalyst, wherein an NOx sensor is disposed in an exhaust pipe of an internal combustion engine at a location downstream of the NOx occlusion catalyst, said NOx sensor comprising a first measurement space having a first oxygen-pumping cell and an oxygen-concentration-measuring cell and communicating with a measurement gas via a first diffusion-controlling layer, each of the first oxygen-pumping cell and the oxygen-concentration-measuring cell comprising an oxygen-ion conductive solid electrolyte layer and porous electrodes disposed on opposite surfaces of the oxygen-ion conductive solid electrolyte layer; a second measurement space having a second oxygen-pumping cell and communicating with the first measurement space via a second diffusion-controlling layer, the second oxygen-pumping cell comprising an oxygen-ion conductive solid electrolyte layer and porous electrodes disposed on opposite surfaces of the oxygen-ion conductive solid electrolyte layer; and a heater for heating the cells to a predetermined active temperature.

The method comprises applying a first pumping current to the first oxygen-pumping cell so that an output voltage from the oxygen-concentration-measuring cell achieves a predetermined value, thereby controlling the concentration of oxygen in the first measurement space at a constant level; at the same time, applying a constant voltage to the second oxygen-pumping cell in a direction such that oxygen is pumped out from the second measurement space; detecting a second pumping current which flows through the second oxygen-pumping cell according to the concentration of NOx in the measurement gas; and if an increase of the second pumping current equal to a predetermined value is detected after start of operation control of the internal combustion engine at a lean air-fuel ratio, judging that the occlusion capability of the NOx occlusion catalyst has deteriorated.

In the detection method described above, the NOx sensor is operated in a manner similar to that used for measuring NOx concentration. Also, the second pumping current is detected, which flows through the second oxygen-pumping cell according to the concentration of NOx contained in the measurement gas.

During operation control at a lean air-fuel ratio, in which exhaust gas containing a large amount of NOx is emitted from an internal combustion engine, NOx contained in the exhaust gas is accumulated in the NOx occlusion catalyst in the form of nitrate. As the thus-accumulated nitrate increases, the occlusion capability of the NOx occlusion catalyst gradually decreases. As a result, leakage of NOx from the NOx occlusion catalyst (namely, the NOx concentration in the measurement gas) increases, resulting in an increase in the second pumping current.

As described above, the second pumping current offset is affected by the oxygen concentration in the first measurement space, and the oxygen concentration in the first measurement space, in turn, is affected by the oxygen concentration in the measurement gas, or air-fuel ratio. Accordingly, the offset current depends on the air-fuel ratio. In the detection method of the present invention, the function of the NOx occlusion catalyst is judged by determining whether the second pumping current has increased by a predetermined value after start of operation control at a lean air-fuel ratio, namely, by using a relative value of the second pumping current rather than an absolute value of the second pumping current. If so, then the occlusion capability of the NOx occlusion catalyst is judged to have deteriorated.

According to the present invention, so long as during detection the air-fuel ratio of a measurement gas does not vary greatly due to, for example, an abrupt change in operating conditions of an internal combustion engine, the influence of the offset can be reliably removed, thereby allowing for an accurate judgment on the functional condition of the NOx occlusion catalyst. Based on the result of this judgment, a refreshing operation for removing nitrate, for example, can be performed only as needed, thereby improving the fuel consumption and efficiency of an internal combustion engine.

In another embodiment, the present invention provides:
(2) A method for detecting a functional condition of an NOx occlusion catalyst, in which an NOx sensor similar to that described in (1) above is disposed in an exhaust pipe of an internal combustion engine at a location downstream of the NOx occlusion catalyst.

The method comprising applying a first pumping current to the first oxygen-pumping cell so that the output voltage from the oxygen-concentration-measuring cell achieves a predetermined value, thereby controlling the concentration of oxygen in the first measurement space at a constant level; at the same time, applying a constant voltage to the second oxygen-pumping cell in a direction such that oxygen is pumped out from the second measurement space; detecting a second pumping current which flows through the second oxygen-pumping cell according to the concentration of NOx contained in the measurement gas; and if a rate of increase of the second pumping current greater than an allowable value is detected after start of operation control of the internal combustion engine at a lean air-fuel ratio, judging that an anomaly has occurred in the occlusion capability of the NOx occlusion catalyst.

As described above, as NOx accumulates in the NOx occlusion catalyst, leakage of NOx from the NOx occlusion catalyst increases. Accordingly, the second pumping current flowing through the second oxygen-pumping cell increases. When any anomaly occurs, for example, when sulfate accumulates in the NOx occlusion catalyst or when an NOx storage material exfoliates, the nitrate occlusion capability of the NOx occlusion catalyst deteriorates, resulting in an increase in the rate of leakage of NOx from the NOx occlusion catalyst. As a result, the rate of increase of the second pumping current increases. Thus, by examining the rate of increase of the second pumping current, or the slope of the second pumping current, it is possible to detect anomalies suffered by the NOx occlusion catalyst.

Based on the result of this judgment, a refreshing operation for removing sulfate, for example, can be performed only as needed. Because unnecessary burdens are not imposed on the NOx occlusion catalyst, the durability of the apparatus can be improved. Also, for example, when an anomaly is not eliminated even though a refreshing operation for removing sulfate is executed, this indicates the occurrence of an anomaly that cannot be eliminated through refreshment, such as exfoliation of an NOx storage material.

In yet another embodiment, the present invention provides:
(3) An apparatus for detecting a functional condition of an NOx occlusion catalyst, comprising an NOx sensor disposed in an exhaust pipe of an internal combustion engine at a location downstream of the NOx occlusion catalyst, the NOx sensor comprising a first measurement space having a first oxygen-pumping cell and an oxygen-concentration-measuring cell and communicating with a measurement gas via a first diffusion-controlling layer, each of the first oxygen-pumping cell and the oxygen-concentration-measuring cell comprising an oxygen-ion conductive solid electrolyte layer and porous electrodes disposed on opposite surfaces of the oxygen-ion conductive solid electrolyte layer; a second measurement space having a second oxygen-pumping cell and communicating with the first measurement space via a second diffusion-controlling layer, the second oxygen-pumping cell comprising an oxygen-ion conductive solid electrolyte layer and porous electrodes disposed on opposite surfaces of the oxygen-ion conductive solid electrolyte layer; and a heater for heating the cells to a predetermined active temperature, said apparatus further comprising:
first pumping-current control means for controlling the concentration of oxygen in said first measurement space at a constant level by applying a first pumping current to the first oxygen-pumping cell such that an output voltage from the oxygen-concentration-measuring cell is maintained at a constant value;

a constant-voltage application source for applying a constant voltage to the second oxygen-pumping cell in a direction such that oxygen is pumped out from the second measurement space;

second pumping-current detection means for detecting a second pumping current which flows through said second oxygen-pumping cell according to the concentration of NOx in the measurement gas; and functional deterioration judgment means for judging that the occlusion capability of the NOx occlusion catalyst has deteriorated when an increase of the second pumping current equal to a predetermined value is detected after start of operation control of the internal combustion engine at a lean air-fuel ratio.

The detection apparatus of the present invention is an apparatus for carrying out the detection method described in (1) above. Specifically, first, the first pumping-current control means causes the first pumping current to flow through the first oxygen-pumping cell such that the output voltage from the oxygen-concentration-measuring cell is maintained at a constant value, thereby controlling the concentration of oxygen in the first measurement space to a constant level. The constant-voltage application means applies a constant voltage to the second oxygen-pumping cell in a direction such that oxygen is pumped out from the second measurement space. The second pumping-current detection means detects the second pumping current flowing through the second oxygen-pumping cell. When the functional deterioration judgment means detects an increase in the second pumping current equal to a predetermined value after start of operation control of the internal combustion engine at a lean air-fuel ratio where the ratio of oxygen to fuel is relatively large, the judgment means judges that the occlusion capability of the NOx occlusion catalyst has deteriorated.

Accordingly, the detection apparatus described in (3) above provides a means for carrying out the detection method described in (1). Furthermore, the detection apparatus (3) can simply and accurately detect a functional deterioration of the NOx occlusion catalyst based on a relative value of the second pumping current, thereby improving the fuel consumption and efficiency of an internal combustion engine.

Normally, operation control at a lean air-fuel ratio is performed during stable operating conditions, such as during operation at a constant speed. However, when operating conditions vary due to, for example, a driver's operation of an accelerator or variations in road conditions, the concentration of oxygen contained in a measurement gas (air-fuel ratio) varies temporarily. As a result, the offset current of the second oxygen-pumping cell which depends on the air-fuel ratio varies according to changes in the air-fuel ratio. Thus, even when a relative value of the second pumping current is obtained, the influence of the offset current cannot be completely removed, thereby reducing the judgment accuracy of the functional deterioration judgment means.

To cope with the above problem, according to yet another embodiment of the present invention, the detection apparatus described in (3) above further comprises:

(4) An oxygen concentration detection means for detecting the concentration of oxygen in the measurement gas based on the first pumping current flowing through the first oxygen-pumping cell; and first correction means for correcting the second pumping current detected by the second pumping-current detection means due to variation in offset current of the second oxygen-pumping cell based on the oxygen concentration detected by the oxygen concentration detection means.

In the thus-configured detection apparatus of the present invention, the oxygen concentration detection means detects the concentration of oxygen contained in a measurement gas based on the first pumping current flowing through the first oxygen-pumping cell. The first correction means compensates for an offset variation included in the detection result by correcting the detection result according to the detected oxygen concentration.

Notably, pumping-current control means for controlling the concentration of oxygen contained in the first measurement space by controlling the current flowing through the first pumping cell is similar to that performed in measuring the concentration of oxygen contained in a measurement gas using a known full-region air-fuel ratio sensor, in which a measurement space with measurement gas diffusion limitations has a pumping cell and an oxygen-concentration-measuring cell. Because the pumping current flowing through the first pumping cell is proportional to the concentration of oxygen contained in the measurement gas, the oxygen concentration can be measured based on the pumping current.

Thus, according to the above embodiment of the present invention, even when the concentration of oxygen contained in the measurement gas varies with operating conditions, such that the offset current of the second oxygen-pumping cell varies with the change in oxygen concentration, the offset variation is compensated to thereby enable highly accurate detection of a functional deterioration of the NOx occlusion catalyst.

Also, in the present invention, the NOx sensor itself, not another sensor, is used for detecting the oxygen concentration. Accordingly, environmental variations influencing the second pumping current can be accurately detected, so that the second pumping current can be accurately compensated therefor.

As described above, the offset current of the second oxygen-pumping cell depends on the concentration of oxygen contained in the measurement gas (air-fuel ratio). Furthermore, the offset current is temperature dependent. That is, the offset current has a temperature characteristic. As shown in FIG. 13, when the element temperature of the NOx sensor deviates from a target control temperature, the oxygen concentration dependency of the offset increases. FIG. 13 is a graph showing the temperature characteristic of the offset current as the oxygen concentration is varied. In FIG. 13, the line with the black diamonds shows offset current for $O_2=0\%$, the line with the squares shows offset current for $O_2=10\%$, and the line with the triangles shows offset current for $O_2=15\%$.

To cope with the above temperature characteristic, according to yet another embodiment of the present invention, the detection apparatus described in (3) above further comprises:

(5) temperature detection means for detecting the temperature of the NOx sensor; and second correction means for correcting the second pumping current detected by the second pumping-current detection means based on the temperature of the NOx sensor detected by the temperature detection means.

In the above embodiment of the present invention, the temperature detection means detects the temperature of the NOx sensor, and the second correction means corrects the second pumping-current detected by the second pumping-current detection means according to the temperature of the NOx sensor detected by the temperature detection means, to thereby compensate for changes in temperature.

Thus, according to the above embodiment of the present invention, even when the temperature of the NOx sensor varies temporarily with operating conditions, such that the offset current of the second oxygen-pumping cell varies with the change in temperature, the offset variation is compensated to thereby enable even more highly accurate detection of a functional deterioration of the NOx occlusion catalyst.

Notably, the detection system may be configured such that judgment by the functional deterioration judgment means is stopped when the oxygen concentration or the temperature of the NOx sensor varies greatly beyond a range allowing for accurate correction. This prevents the occurrence of an erroneous judgment.

When operation control of an internal combustion engine at a lean air-fuel ratio begins, the concentration of oxygen contained in the measurement gas increases. As described above, the first pumping current is proportional to the concentration of oxygen contained in the measurement gas. Thus, in accordance with yet another embodiment of the present invention, the functional deterioration judgment means comprises:

(6) means for detecting the start of operation control of the internal combustion engine at a lean air-fuel ratio by detecting a variation in said first pumping current.

In this case, because variation in the concentration of oxygen contained in the measurement gas is detected using the NOx sensor itself, the functional deterioration judgment means can be operated in quick response to an environmental variation influencing the second pumping current.

In yet another embodiment, the present invention provides:

(7) An apparatus for detecting a functional condition of an NOx occlusion catalyst, in which an NOx sensor similar to that described in (3) above is disposed in an exhaust pipe of an internal combustion engine at a location downstream of the NOx occlusion catalyst, said apparatus comprising:

first pumping-current control means for controlling the concentration of oxygen in the first measurement space to a constant level by applying a first pumping current to the first oxygen-pumping cell such that an output voltage from the oxygen-concentration-measuring cell is maintained at a constant value;

constant-voltage application means for applying a constant voltage to the second oxygen-pumping cell in a direction such that oxygen is pumped out from the second measurement space;

second pumping-current detection means for detecting a second pumping current which flows through the second oxygen-pumping cell according to the concentration of NOx in the measurement gas; and functional anomaly judgment means for judging that an anomaly has occurred in the occlusion capability of the NOx occlusion catalyst when a rate of increase of the second pumping current greater than an allowable value is detected after start of operation control of the internal combustion engine at a lean air-fuel ratio.

The detection apparatus described in (7) is an apparatus for carrying out the detection method described in (2) above. Specifically, the first pumping-current control means causes the first pumping current to flow through the first oxygen-pumping cell such that the output voltage from the oxygen-concentration-measuring cell is maintained at a constant value, thereby controlling the concentration of oxygen contained in the first measurement space to a constant value. The constant-voltage application means applies a constant voltage to the second oxygen-pumping cell in a direction such that oxygen is pumped out from the second measurement space. The second pumping-current detection means detects the second pumping current flowing through the second oxygen-pumping cell. When the functional anomaly judgment means detects that the second pumping current is increasing at a rate exceeding an allowable value after start of operation control of the internal combustion engine at a lean air-fuel ratio where the ratio of oxygen to fuel is relatively large, the judgment means determines that an anomaly has occurred in the occlusion capability of the NOx occlusion catalyst.

Accordingly, the above embodiment of the present invention provides an apparatus for carrying out the detection method described in (2) above, and can simply and accurately detect an anomaly in the NOx occlusion catalyst, such as accumulation of sulfate and exfoliation of an NOx storage material, based on a change in the second pumping current per unit time, thereby improving the fuel consumption and efficiency of an internal combustion engine and the durability of the apparatus.

The allowable value may be set based on NOx leakage from the NOx occlusion catalyst, which is estimated based on the NOx occlusion capability of the NOx occlusion catalyst and the concentration of NOx in exhaust gas emitted from the internal combustion engine.

As the concentration of NOx contained in exhaust gas flowing through to the NOx occlusion catalyst increases, or even at the same NOx concentration, as the flow rate of exhaust gas flowing into the NOx occlusion catalyst increases, the amount of NOx stored in the NOx occlusion catalyst is increased. Variation of the second pumping current with respect to time (i.e., slope), which is determined by the second pumping current detection means, also varies according to the condition of the exhaust gas flowing into the NOx occlusion catalyst.

To cope with the above tendency, in accordance with yet another embodiment of the present invention, the detection apparatus described in (7) above further comprises:

(8) inflow gas conditions detection means for detecting the flow rate of exhaust gas flowing into the NOx occlusion catalyst and the concentration of NOx in the exhaust gas; and allowable value setting means for setting the allowable value based on the inflow gas conditions detected by the inflow gas conditions detection means such that the allowable value is set higher as the flow rate of the exhaust gas increases or as the concentration of NOx in the exhaust gas increases.

By setting an optimum allowable value according to the flow rate of exhaust gas flowing into the NOx occlusion catalyst and the NOx concentration of the exhaust gas, an anomaly in the NOx occlusion catalyst can be detected with far better accuracy.

The concentration of NOx contained in the inflow exhaust gas and the flow rate of the inflow exhaust gas are closely related to the operating conditions of an internal combustion engine, such as engine speed and a negative pressure within a suction pipe. Thus, in yet another embodiment of the present invention, the inflow gas conditions detection means comprises:

(9) means for estimating the flow rate of the exhaust gas and the concentration of NOx contained in the exhaust gas based on operating conditions of the internal combustion engine.

In this case, various parameters used to control the internal combustion engines can be utilized with no need for employing additional means for measuring the conditions of the exhaust gas flowing into the NOx occlusion catalyst. Thus, the accuracy of the detection apparatus can be improved in a simple manner.

Next, in accordance with yet another embodiment of the present invention, in the detection apparatus described in any of (7) to (9) above, the functional anomaly judgment means comprises:

(10) current-increasing-time measuring means for measuring a time required for the second pumping current to increase by a predetermined value after start of operation control of the internal combustion engine at a lean air-fuel ratio, wherein a smaller value measured by the current-increasing-time measuring means indicates that the second pumping current is increasing at a higher rate (i.e., a larger increase in the second pumping current per unit time).

Also, in yet another embodiment of the present invention, the functional anomaly judgment means comprises:

(11) current-increase measuring means for measuring an increase of the second pumping current during a predetermined period of time after start of operation control of the internal combustion engine at a lean air-fuel ratio, wherein a larger value measured by the current-increase measuring means indicates that the second pumping current is increasing at a higher rate (i.e., a larger increase in the second pumping current per unit time).

That is, the rate of increase or slope of the second pumping current may be obtained based on the time required to increase the second pumping current by a predetermined value, or based on an increase in the second pumping current as measured over a predetermined period of time.

Next, in accordance with yet another embodiment of the present invention, the detection apparatus described in an any of (7) to (11) above further comprises:

(12) oxygen concentration detection means for detecting the concentration of oxygen in the measurement gas based on the first pumping current flowing through the first oxygen-pumping cell; and first correction means for correcting the second pumping current detected by the second pumping-current detection means due to variation in offset current of the second oxygen-pumping cell based on the oxygen concentration detected by the oxygen concentration detection means.

In accordance with yet another embodiment of the present invention, the detection apparatus described in (7) to (11) above further comprises:

(13) temperature detection means for detecting the temperature of the NOx sensor; and second correction means for correcting the second pumping current detected by the second pumping-current detection means due to variation in temperature based on the temperature of the NOx sensor detected by the temperature detection means.

In yet another embodiment, in the detection apparatus described in any of (7) to (11), the functional anomaly judgment means comprises:

(14) means for detecting the start of operation control of the internal combustion engine at a lean air-fuel ratio by detecting a variation in the first pumping current.

The detection apparatus described in (12), (13) and (14) are similar to those described in (4), (5) and (6) for carrying out the detection method described in (1) above, and yield effects similar to those provided by the detection apparatus described in (4), (5) and (6), as described above.

Accordingly, the detection apparatus described in (12) above can accurately compensate the second pumping current for variation in the oxygen concentration of a measurement gas, and thus can determine a functional anomaly in the NOx occlusion catalyst with high accuracy.

The detection apparatus described in (13) above can compensate the second pumping current for variation in the temperature of the NOx sensor, and thus can determine a functional anomaly in the NOx occlusion catalyst with higher accuracy.

The detection apparatus described in (14) above allows the functional anomaly judgment means to operate in quick response to environmental variations influencing the second pumping current.

In accordance with yet another embodiment, the present invention provides:

(15) An apparatus for detecting a functional condition of an NOx occlusion catalyst, comprising an NOx sensor disposed in an exhaust pipe of an internal combustion engine at a location downstream of the NOx occlusion catalyst, the NOx sensor including a first measurement space having a first oxygen-pumping cell and an oxygen-concentration-measuring cell and communicating with a measurement gas via a first diffusion-controlling layer, each of the first oxygen-pumping cell and the oxygen-concentration-measuring cell comprising an oxygen-ion conductive solid electrolyte layer and porous electrodes disposed on opposite surfaces of the oxygen-ion conductive solid electrolyte layer; a second measurement space having a second oxygen-pumping cell and communicating with the first measurement space via a second diffusion-controlling layer, the second oxygen-pumping cell comprising an oxygen-ion conductive solid electrolyte layer and porous electrodes disposed on opposite surfaces of the oxygen-ion conductive solid electrolyte layer; and a heater for heating the cells to a predetermined active temperature, said apparatus comprising:

first pumping-current control means for controlling the concentration of oxygen in the first measurement space at a constant level by applying a first pumping current to the first oxygen-pumping cell such that an output voltage from the oxygen-concentration-measuring cell is maintained at a constant value;

constant-voltage application means for applying a constant voltage to the second oxygen-pumping cell in a direction such that oxygen is pumped out from the second measurement space;

second pumping-current detection means for detecting a second pumping current which flows through the second oxygen-pumping cell according to the concentration of NOx contained in the measurement gas;

minimum value detection means for detecting a minimum value of the second pumping current during a predetermined waiting time after start of operation control of the internal combustion engine at a lean air-fuel ratio; and functional condition judgment means for judging a functional condition of the NOx occlusion catalyst based on a relative value calculated as the difference between a value of the second pumping current detected by the second pumping-current detection means after elapse of the waiting time and the minimum value of the second pumping current detected by the minimum value detection means.

In the thus-configured detection apparatus of the present invention, the first pumping-current control means causes the first pumping current to flow through the first oxygen-pumping cell such that the output voltage from the oxygen-concentration-measuring cell is maintained at a constant value, thereby controlling the concentration of oxygen contained in the first measurement space to a constant level. The constant-voltage application means applies a constant voltage to the second oxygen-pumping cell in a direction such that oxygen is pumped out from the second measurement space. That is, the NOx sensor is operated in a normal manner so as to measure the NOx concentration. At this time, the second pumping-current detection means detects the second pumping current which flows through the second oxygen-pumping cell according to the concentration of NOx in the measurement gas.

Notably, during operation control at a lean air-fuel ratio, in which exhaust gas containing a large amount of NOx is emitted from an internal combustion engine, NOx contained in the exhaust gas is accumulated on the NOx occlusion catalyst in the form of nitrate. As the thus-accumulated nitrate increases, the occlusion capability of the NOx occlusion catalyst gradually decreases. As a result, leakage of NOx from the NOx occlusion catalyst (i.e., the NOx concentration in the measurement gas) increases, resulting in an increase in the second pumping current. Since the second pumping current varies according to a functional condition of the NOx occlusion catalyst, the functional condition can be judged from the second pumping current.

Particularly, in the above embodiment of the present invention, the minimum value detection means detects a minimum value of the second pumping current during a predetermined waiting time after start of operation control of the internal combustion engine at a lean air-fuel ratio. Also, the functional condition judgment means judges a functional condition of the NOx occlusion catalyst based on a relative value between the detected minimum value of the second pumping current and a value of the second pumping current detected by the second pumping-current detection means after elapse of the waiting time. Preferably, the waiting time is set to a sufficient length so as to allow sufficient settlement of variation in the second pumping current associated with a large variation of the concentration of oxygen in the exhaust gas observed immediately after operation control at a theoretical air-fuel ratio is switched to operation control at a lean air-fuel ratio.

As described above, according to the detection apparatus of the above embodiment of the present invention, instead of an absolute value of the second pumping current, a relative value of the second pumping current detected immediately after start of operation control at a lean air-fuel ratio is used for judging a functional condition of the NOx occlusion catalyst; thus, the judgment can be performed more accurately.

Furthermore, a minimum value of the second pumping current detected immediately after start of operation control at a lean air-fuel ratio is used as a reference value in calculating the above relative value. Thus, even when, due to excessive deterioration of the occlusion capability of the NOx occlusion catalyst, the second pumping current has already increased greatly at the time of elapse of the waiting time, a functional condition of the NOx occlusion catalyst can be reliably judged.

Thus, by using the detection apparatus of the above embodiment of the present invention, the reliability of an exhaust gas purification system using an NOx occlusion catalyst can be improved.

In accordance with another embodiment, the detection apparatus described in (15) above is characterized in that:

(16) the minimum value detection means comprises means for detecting the start of operation control of the internal combustion engine at a lean air-fuel ratio based on variation in the first pumping current.

The first pumping-current control means, which controls the concentration of oxygen in the first measurement space to a constant level by applying the first pumping current to the first oxygen-pumping cell such that the output voltage from the oxygen-concentration-measuring cell is maintained at a constant value, controls in a manner identical to that of a known oxygen sensor not having a second oxygen-pumping cell. Accordingly, the first pumping current becomes proportional to the concentration of oxygen in the measurement gas. Because the concentration of oxygen in the measurement gas increases during operation control at a lean air-fuel ratio as compared with the case of operation control at a theoretical air-fuel ratio, start of operation control at a lean air-fuel ratio can be detected based on the first pumping current.

As described above, in the detection apparatus of the present invention, the NOx sensor itself, not another sensor, is used for detecting the oxygen concentration. Accordingly, environmental variations affecting the second pumping current can be accurately detected, so that the second pumping current (an offset of the second pumping current) can be managed with accuracy and speed.

In the detection apparatus described in (15) or (16), the functional condition judgment means may comprise:

(17) means for judging that the occlusion capability of said NOx occlusion catalyst had deteriorated when the relative value of the second pumping current exceeds a predetermined value.

Alternatively, the functional condition judgment means may comprise:

(18) means for judging that an anomaly has occurred in the occlusion capability of said NOx occlusion catalyst when a time-course variation rate of the relative value of the second pumping current becomes greater than a predetermined allowable value.

DESCRIPTION OF SYMBOLS

Figure 1:
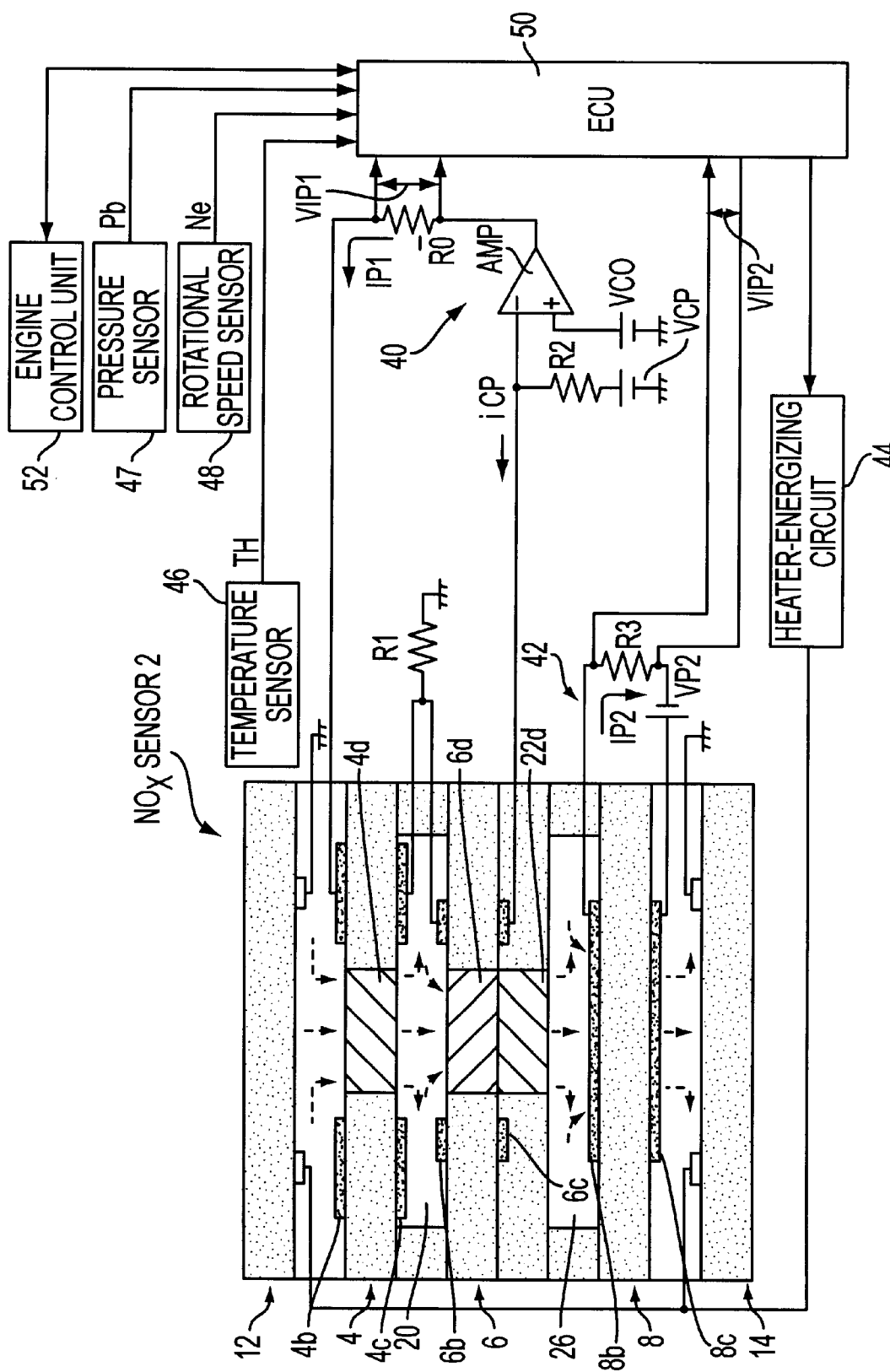
FIG. 1 is a schematic diagram showing the entire configuration of an apparatus for detecting a functional condition of an NOx occlusion catalyst according to an embodiment of the present invention.

2: NOx sensor
4: first oxygen-pumping cell
6: oxygen-concentration-measuring cell
8: second oxygen-pumping cell
12: heater
18, 22, 24: solid electrolyte layers
20: first measurement space
26: second measurement space
28: spacer
40: drive circuit
42: sensing circuit
44: heater-energizing circuit
46: temperature sensor 47: pressure sensor
48: rotational speed sensor
50: ECU—electronic control unit
52: engine control unit
S1: internal combustion engine
S2: exhaust pipe
S3: NOx occlusion catalyst
S4: suction pipe

DETAILED DESCRIPTION OF THE PREFERRED EMBODIMENTS

Figure 2:
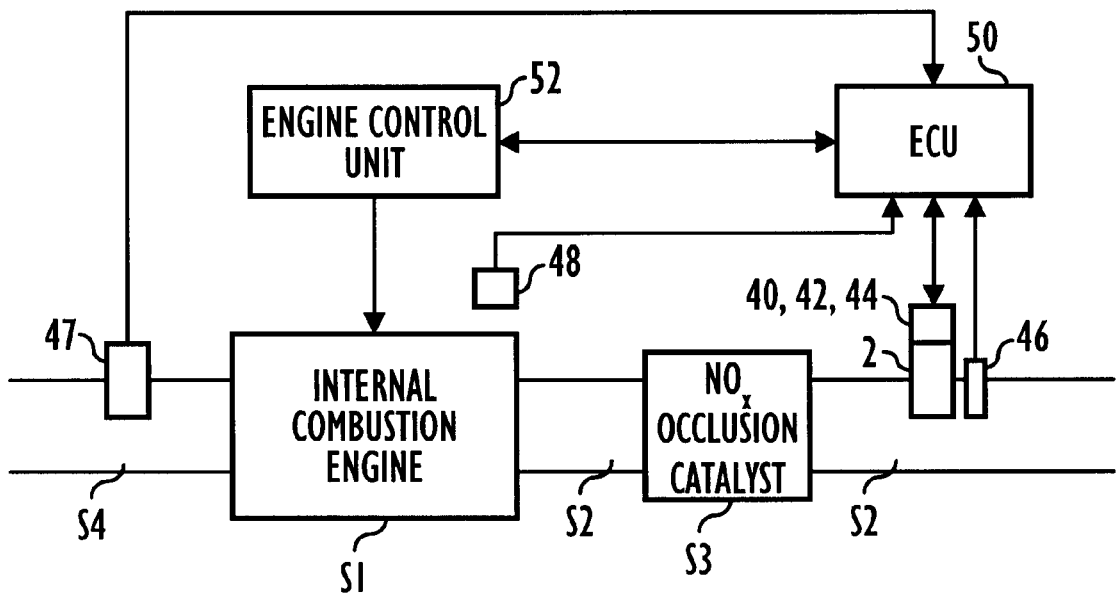
FIG. 2 is a diagram showing an installation location for the NOx sensor of the embodiment of FIG. 1.
Figure 3:
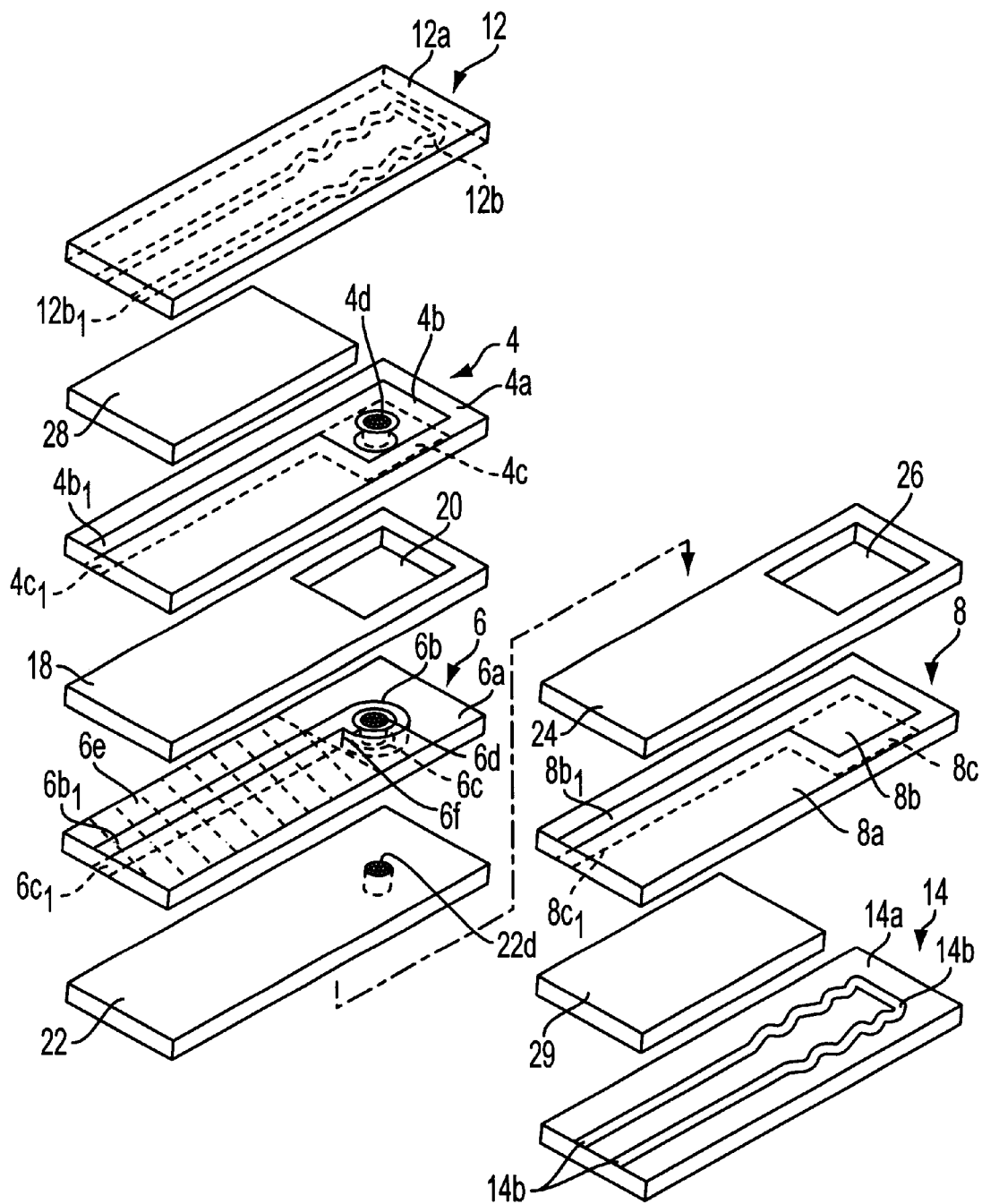
FIG. 3 is an exploded perspective view of the NOx sensor of the embodiment of FIG. 1.

The present invention will next be described in greater detail with reference to drawings, however, the present invention should not be construed as being limited thereto.
First Embodiment FIG. 1 is a schematic diagram showing the entire configuration of an apparatus for detecting a functional condition of an NOx (NOx) occlusion catalyst according to a first embodiment of the present invention. FIG. 2 is a diagram showing an installation location for an NOx sensor 2 used in the detection apparatus. FIG. 3 is an exploded perspective view of the NOx sensor 2.

As shown in FIGS. 1 and 2, the detection apparatus of the present embodiment includes an NOx sensor 2 mounted in an exhaust pipe S2 attached to an internal combustion engine S1 of a vehicle at a location downstream of an NOx occlusion catalyst S3; a drive circuit 40 for applying current to a first oxygen-pumping cell (hereinafter referred to as a first pumping cell) 4 and an oxygen-concentration-measuring cell (hereinafter referred to as a Vs cell) 6 of the NOx sensor 2 and for detecting current (hereinafter referred to as first pumping current) IPI which flows to the first pumping cell 4; a sensing circuit 42 for applying a constant voltage to the second pumping cell 8 and for detecting current (hereinafter referred to as second pumping current) IP2 which flows to a second oxygen-pumping cell (hereinafter referred to as a second pumping cell) 8 of the NOx sensor 2; a heater-energizing circuit 44 for heating the cells 4, 6 and 8 by applying current to a pair of heaters 12 and 14 of the NOx sensor 2; a temperature sensor 46 for detecting temperature TH in the vicinity of the NOx sensor 2; a pressure sensor 47 for measuring a negative pressure Pb in a suction pipe S4 attached to the internal combustion engine S1; a rotational speed sensor 48 for detecting a rotational speed Ne (hereinafter referred to as engine speed) of an output shaft of the internal combustion engine S1; and an electronic control unit (hereinafter referred to as ECU) 50, which includes a microcomputer, for controlling the drive circuit 40 and the heater-energizing circuit 44 and for detecting a functional condition of the NOx occlusion catalyst S3 based on detection signals VIP1 and VIP2 issued from the drive circuit 40 and the sensing circuit 42, respectively, and detection signals TH, Pb and Ne issued from the sensors 46, 47 and 48, respectively.

The detection apparatus of the present embodiment receives operation control information indicative of execution of operation control at a lean air-fuel ratio from an engine control unit 52. The engine control unit 52 controls the operating conditions of the internal combustion engine S1 such that a lean air-fuel ratio is effected while operating conditions are stable, as in the case of travel at a constant speed, and a theoretical air-fuel ratio is effected in other cases.

Herein, exhaust gas flowing through the exhaust pipe S2 is referred to as follows: gas emitted from the internal combustion engine S1 and flowing into the NOx occlusion catalyst S3 is referred to as exhaust gas, whereas gas flowing out from the NOx occlusion catalyst S3 is referred to as a measurement gas.

Next, as shown in FIG. 3, in the NOx sensor 2, the first pumping cell 4 includes a sheet-like solid electrolyte layer 4a and rectangular porous electrodes 4b and 4c formed on both sides of the solid electrolyte layer 4a. Lead portions 4b1 and 4c1 extend from the porous electrodes 4b and 4c, respectively. Furthermore, a round hole is formed in the solid electrolyte layer 4a so as to penetrate the porous electrodes 4b and 4c at their central portions. The thus-formed round hole is filled with a porous filler to thereby form a diffusion-controlling layer 4d.

The Vs cell 6 includes a sheet-like solid electrolyte layer 6a having the same shape as the solid electrolyte layer 4a of the first pumping cell 4 and circular porous electrodes 6b and 6c formed on both sides of the solid electrolyte layer 6a. Lead portions 6b1 and 6c1 extend from the porous electrodes 6b and 6c, respectively. Furthermore, a round hole is formed in the solid electrolyte layer 6a so as to penetrate the porous electrodes 6b and 6c at their central portions. The thus-formed round hole is filled with a porous filler to thereby form a diffusion-controlling layer 6d.

The porous electrodes 4b and 4c of the first pumping cell 4 and the porous electrodes 6b and 6c of the Vs cell 6 are located on the solid electrolyte layers 4a and 6a, respectively, such that their centers are aligned with each other. Accordingly, when the first pumping cell 4 and the Vs cell 6 are arranged in layers, the diffusion-controlling layers 4d and 6d face each other. The circular porous electrodes 6b and 6c of the Vs cell 6 are arranged around the diffusion-controlling layer 6d and have a size that is smaller than that of the rectangular porous electrodes 4b and 4c of the first pumping cell 4. An insulation film formed of alumina or the like is formed on both surfaces of the Vs cell 6 so as to cover the lead portions 6b1 and 6c1 from the outside in order to prevent current leakage from the lead portions 6b1 and 6c1. Furthermore, a leakage resistance portion 6f is formed between the lead portions 6b1 and 6c1 in order to leak part of pumped-out oxygen from the side of the porous electrode 6c to the side of the porous electrode 6b.

The first pumping cell 4 and the Vs cell 6 are arranged in layers with a solid electrolyte layer 18 interposed therebetween. The solid electrolyte layer 18 has the same shape as that of the solid electrolyte layers 4a and 6a. The solid electrolyte layer 18 has a rectangular hole formed therein in a position corresponding to the porous electrodes 4c and 6b and having a size greater than that of the porous electrode 4c. The thus-formed rectangular hole serves as a first measurement space 20.

Also, a solid electrolyte layer 22, which has the same shape as that of the solid electrolyte layers 4a and 6a, is placed on the Vs cell 6 on the side of the porous electrode 6c. The solid electrolyte layer 22 has a round hole formed therein in a position corresponding to the diffusion-controlling layer 6d of the Vs cell 6 and having the same size as that of the diffusion-controlling layer 6d. The thus-formed round hole is filled with a porous filler to thereby form a diffusion-controlling layer 22d.

As in the first pumping cell 4, the second pumping cell 8 includes a sheet-like solid electrolyte layer 8a and rectangular porous electrodes 8b and 8c formed on both sides of the solid electrolyte layer 8a. Lead portions 8b1 and 8c1 extend from the porous electrodes 8b and 8c, respectively. The second pumping cell 8 and the solid electrolyte layer 22 are arranged in layers with a solid electrolyte layer 24 interposed therebetween. The solid electrolyte layer 24 is formed in the same manner as the solid electrolyte layer 18.

As a result, a rectangular hole formed in the solid electrolyte layer 24 serves as a second measurement space 26.

The above components of the NOx sensor 2 excluding the heaters 12 and 14 are united in layers and subsequently sintered at a predetermined temperature, yielding the NOx sensor 2.

The heaters 12 and 14 are placed on opposite sides of the above-described laminate of the first pumping cell 4, the Vs cell 6 and the second pumping cell 8, namely, outside the first pumping cell 4 and the second pumping cell 8, respectively, such that a predetermined gap is formed between each of the heaters 12 and 14 and the laminate using spacers 28 and 29.

The heater 12 (14) includes a heater substrate 12a (14a) having a shape same as that of the solid electrolyte layers 4a, 6a and 8a, a heater wiring 12b (14b) formed on the heater substrate 12a (14a) on the side facing the cell 4 (8), and a lead portion 12b1 (14b) extending from the heater wiring 12b (14b). The spacer 28 (29) is interposed between the heater 12 (14) and the first pumping cell 4 (second pumping cell 8) at a position corresponding to the lead portion 12b1 so that the heater wiring 12b (14b) faces the porous electrode 4b (8c) of the first pumping cell 4 (second pumping cell 8) with a gap formed therebetween.

The heater substrate 12a (14a) is formed of alumina. The heater wiring is formed by the steps of: blending platinum powder and alumina to obtain a mixture paste; screen-printing a pattern of the paste on an alumina sheet; and firing the sheet. Notably, the heater substrates 12a and 14a and the spacers 28 and 29 are each formed of fired alumina sheets. The heaters 12 and 14 and the first and second pumping cells 4 and 8 are bonded together using a ceramic bonding agent such that the cells 4 and 8 are sandwiched between the heaters 12 and 14, thereby forming the complete NOx sensor 2.

Typical examples of a solid electrolyte forming the solid electrolyte layers 4a, 6a and 8a include a solid solution of zirconia and yttria and a solid solution of zirconia and calcia. Other examples of such a solid electrolyte include a solid solution of hafnia, a solid solution of a perovskite oxide, and a solid solution of a trivalent metal oxide. The porous electrodes provided on the surfaces of the solid electrolyte layers 4a, 6a and 8a are preferably formed of platinum or rhodium having a catalytic function or their alloys. Known methods of forming such a porous electrode include a thick-film forming method and a thermal spraying method. The thick-film forming method includes the steps of: mixing platinum powder and powder of the same material as that of the solid electrolyte layers to obtain a paste; screen-printing the paste onto a solid electrolyte layer; and sintering the solid electrolyte layer. The diffusion-controlling layers 4d, 6d and 22d are preferably formed of ceramics having fine through-holes or porous ceramics.

The heater wirings 12b and 14b of the heaters 12 and 14, respectively, are preferably formed of a composite material of ceramics and platinum or a platinum alloy. The lead portions 12b1 and 14b1 are preferably formed of platinum or a platinum alloy in order to reduce electric loss therein by reducing their resistance. The heater substrates 12a and 14a and the spacers 28 and 29 may be formed of alumina, spinel, forsterite, steatite, zirconia, or a like material.

As shown in FIG. 1, the porous electrode 4c of the first pumping cell 4 and the porous electrode 6b of the Vs cell 6, both of which are located on the side of the first measurement space 20, are grounded via a resistor R1. The other porous electrodes 4b and 6c are connected to the drive circuit 40.

The drive circuit 40 includes a resistor R2 and a differential amplifier AMP. A constant voltage VCP is applied to one end of the resistor R2, and the other end of the resistor R2 is connected to the porous electrode 6c of the Vs cell 6. The negative input terminal of the differential amplifier AMP is connected to the porous electrode 6c of the Vs cell 6 via a switch SW1. A reference voltage VC0 is applied to the positive input terminal of the differential amplifier AMP. The output terminal of the differential amplifier AMP is connected to the porous electrode 4b of the first pumping cell 4 via a resister R0.

The drive circuit 40 operates in the following manner. First, a constant small current iCP is supplied to the Vs cell 6 via the resistor R2 to thereby pump out oxygen from the first measurement space 20 into the porous electrode 6c of the Vs cell 6. Because the porous electrode 6c is blocked by the solid electrolyte layer 22 and communicates with the porous electrode 6b via the leakage resistance portion 6f, the concentration of oxygen in the blocked space of the porous electrode 6c is maintained at a constant level by applying a small current iCP to the Vs cell 6. Thus, the blocked space serves as an internal reference oxygen source.

When the porous electrode 6c of the Vs cell serves as an internal reference oxygen source, an electromotive force is generated in the Vs cell 6 in accordance with the difference in oxygen concentration between the first measurement space 20 and the internal reference oxygen source. As a result, a voltage Vs developed on the side of the porous electrode 6c corresponds to the concentration of oxygen in the first measurement space 20. Because the voltage Vs is input to the differential amplifier AMP, the differential amplifier AMP outputs a voltage in accordance with the deviation of the input voltage from the reference voltage VC0 (VC0—input voltage). The output voltage is applied to the porous electrode 4b of the first pumping cell 4 via the resistor R0.

As a result, a first pumping current IP1 flows to the first pumping cell 4. By controlling the first pumping current IP1, a constant electromotive force is generated by the Vs cell 6 (in other words, the concentration of oxygen in the first measurement space 20 becomes constant).

That is, the drive circuit 40 serves as the pumping-current control means, and controls the concentration of oxygen contained in the first measurement space 20 so as to maintain constant the concentration of oxygen in the measurement gas which has entered into the first measurement space 20 via the diffusion-controlling layer 4d.

The thus-controlled concentration of oxygen in the first measurement space 20 is set such that only a small amount of oxygen (e.g., 1000 ppm) is present, thereby preventing the decomposition of NOx components contained in the measurement gas contained in the first measurement space 20 due to applying the first pumping current IP1 to the first pumping cell 4. The reference voltage VC0 for determining this concentration of oxygen is set at 100 mV to 200 mV. The resistor R0 disposed between the output terminal of the differential amplifier AMP and the porous electrode 4b is adapted to detect the first pumping current IP1. A voltage VIP1 developed across the resistor R0 is input to the ECU 50 as a detection signal corresponding to the first pumping current IP1.

A constant voltage VP2 is applied between the porous electrodes 8b and 8c of the second pumping cell 8 of the NOx sensor 2 via a resistor R3, which is a component of the sensing circuit 42 and serves as the constant-voltage application source of the invention. The constant voltage VP2 is applied to the second pumping cell 8 in a direction such that the porous electrodes 8c and 8b become a positive electrode and a negative electrode, respectively. As a result, current flows from the porous electrode 8c to the porous electrode 8b to thereby pump out oxygen from the second measurement space 26. The constant voltage VP2 is set at a voltage, for example 450 mV, such that the NOx component contained in the measurement gas flowing from the first measurement space 20 to the second measurement space 26 via the diffusion-controlling layers 6d and 22d are decomposed, to thereby pump out an oxygen component from the measurement gas.

The resistor R3 is adapted to convert the second pumping current IP2 flowing through the second pumping cell 8 as a result of applying the constant voltage VP2, to a voltage VIP2, and adapted to input the voltage VIP2 to the ECU 50 as a detection signal corresponding to the second pumping current IP2.

In the apparatus for detecting a functional condition of the NOx occlusion catalyst S3, the control circuit 40 controls the concentration of oxygen in the measurement gas which has entered into the first measurement space 20 via the diffusion-controlling layer (first diffusion-controlling layer) 4d, to a constant level. The measurement gas controlled to a constant oxygen concentration flows from the first measurement space 20 to the second measurement space 26 via the diffusion-controlling layers (second diffusion-controlling layers) 6d and 22d. Accordingly, the first pumping current IP1 flowing through the first pumping cell 4 varies in accordance with the concentration of oxygen in the measurement gas. The second pumping current IP2 flowing through the second pumping cell 8 varies in accordance with the concentration of NOx in the measurement gas. Thus, by reading the detection signals VIP1 and VIP2 corresponding to the first and second pumping currents IP1 and IP2, respectively, and by carrying out a predetermined computation based on the signals thus read, the ECU 50 can determine the concentrations of oxygen and NOx in the measurement gas.

In order to secure accuracy of measuring the oxygen and NOx concentrations, the temperature of the NOx sensor 2 is preferably controlled to a constant level. To meet this requirement, current applied to the heaters 12 and 14 from the heater-energizing circuit 44 is controlled so that the temperature TH detected by the temperature sensor 46 achieves a target temperature.

Figure 4A:
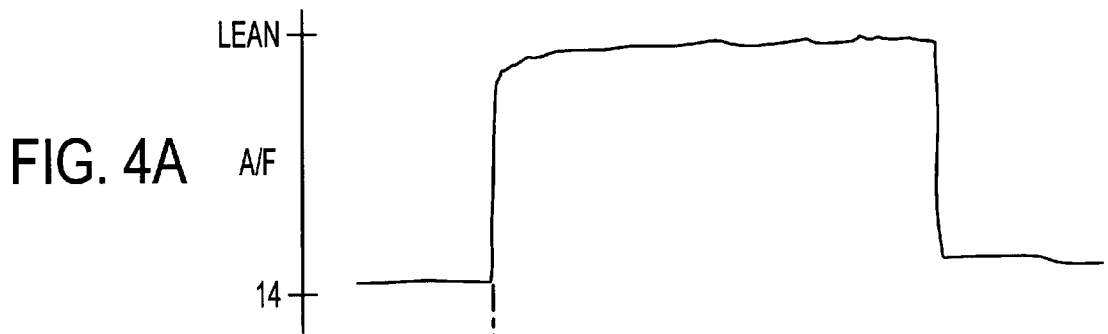
FIGS. 4(a)–(c) are waveform charts of the second pumping current output obtained from the NOx sensor of the embodiment of FIG. 1.
Figure 4B:
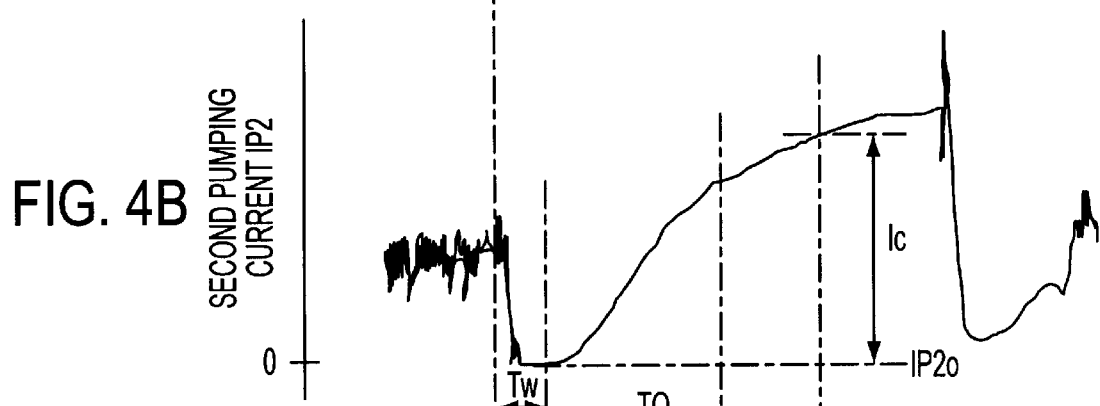
Figure 4C:
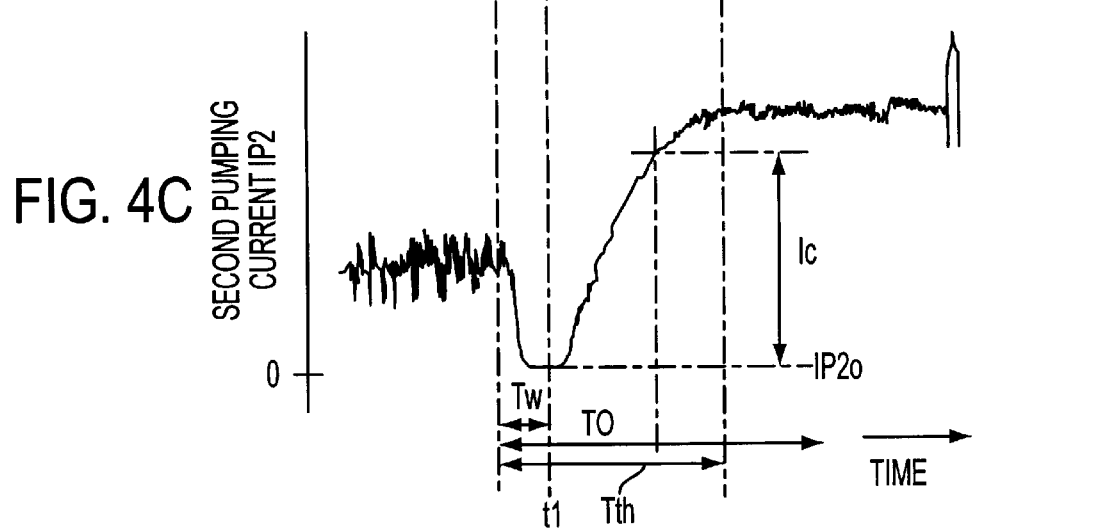
Figure 14A:
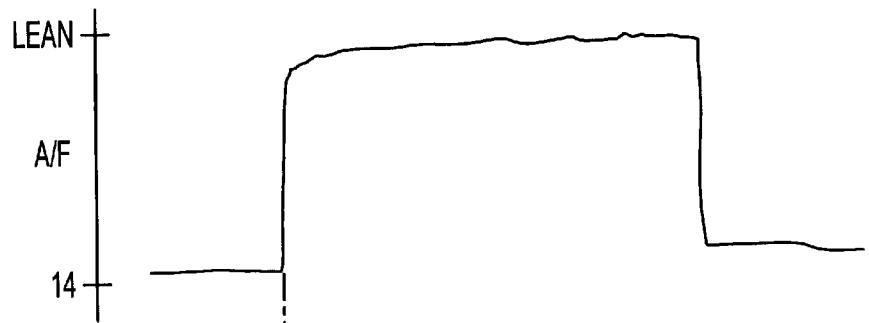
FIGS. 14(a)–(c) are waveform charts of the second pumping current output from the NOx sensor in accordance with the embodiment of FIG. 15.
Figure 14B:
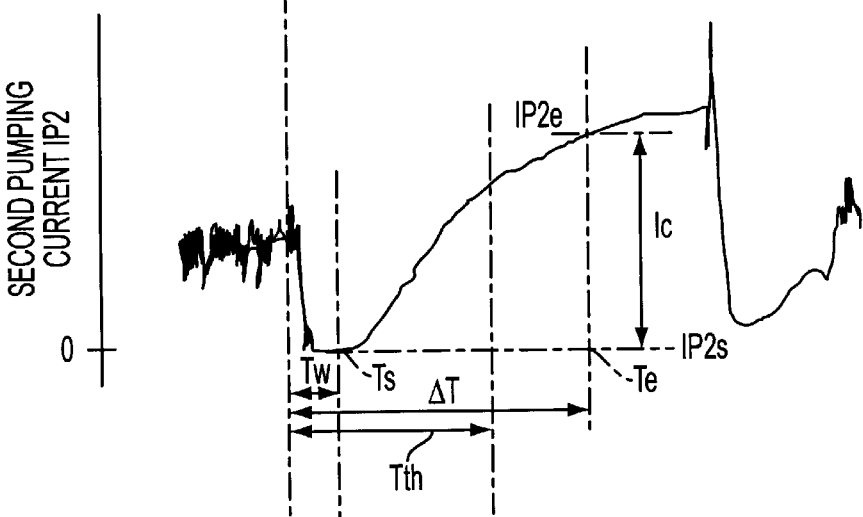
Figure 14C:
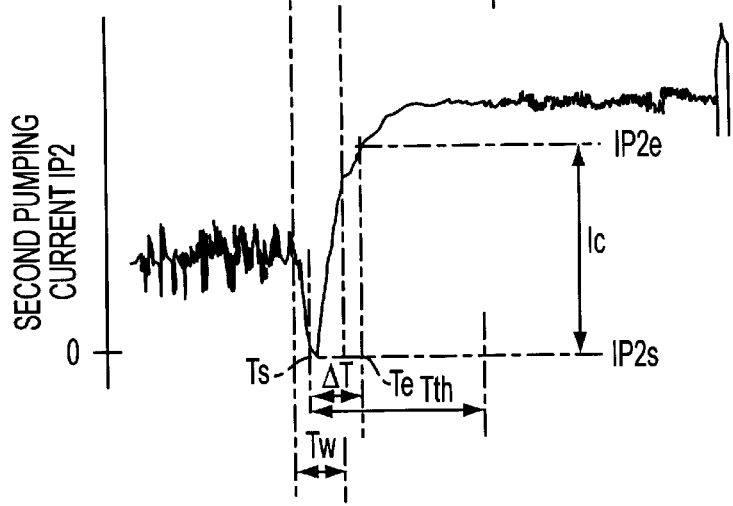

FIGS. 4(a)–(c) and also FIGS. 14(a)–(c) show graphs of the measured second pumping current IP2 of the NOx sensor 2, which is located downstream of the NOx occlusion catalyst S3, when the engine control unit 52 switches the operation control mode of the internal combustion engine S1 from operation control at a theoretical air-fuel ratio (hereinafter referred to as normal control) to operation control at a lean air-fuel ratio (hereinafter referred to as lean control).

As shown in FIGS. 4(a) and 4(b) and also FIGS. 14(a) and 14(b), when the control mode of the internal combustion engine S1 is switched from normal control (A/F (air-fuel ratio)≡14) to lean control, initially, NOx hardly leaks from the NOx occlusion catalyst S3 because the NOx occlusion catalyst S3 has sufficient NOx occlusion capability. Subsequently, as the NOx occlusion capability of the NOx occlusion catalyst S3 deteriorates with an increase in the amount of NOx accumulated on the NOx occlusion catalyst S3 in the form of nitrate, leakage of NOx from the NOx occlusion catalyst S3 toward the downstream side of the NOx occlusion catalyst S3 increases, namely, the concentration of NOx in the measurement gas increases, resulting in an increase in the second pumping current IP2. Finally, when the NOx occlusion catalyst S3 is almost disabled in its ability to store NOx, the concentration of NOx in the measurement gas becomes substantially equal to the concentration of NOx in the exhaust gas flowing into the NOx occlusion catalyst S3.

FIG. 4(c) and FIG. 14(c) show the resulting measurement in the case of fuel containing sulfur, illustrating deterioration in the NOx occlusion capability caused by accumulation of sulfur on the NOx occlusion catalyst S3 in the form of sulfate. As seen from FIG. 4(c) and FIG. 14(c), the rate of increase or slope in the second pumping current IP2 is greater than in FIG. 4(b) and in FIG. 14(b).

The process of detecting a functional condition of the NOx occlusion catalyst S3 by the ECU 50 will next be described using the flowchart of FIG. 5.

This process is repeatedly executed after the NOx sensor 2 is activated by applying current to the heaters 12 and 14.

Figure 5:
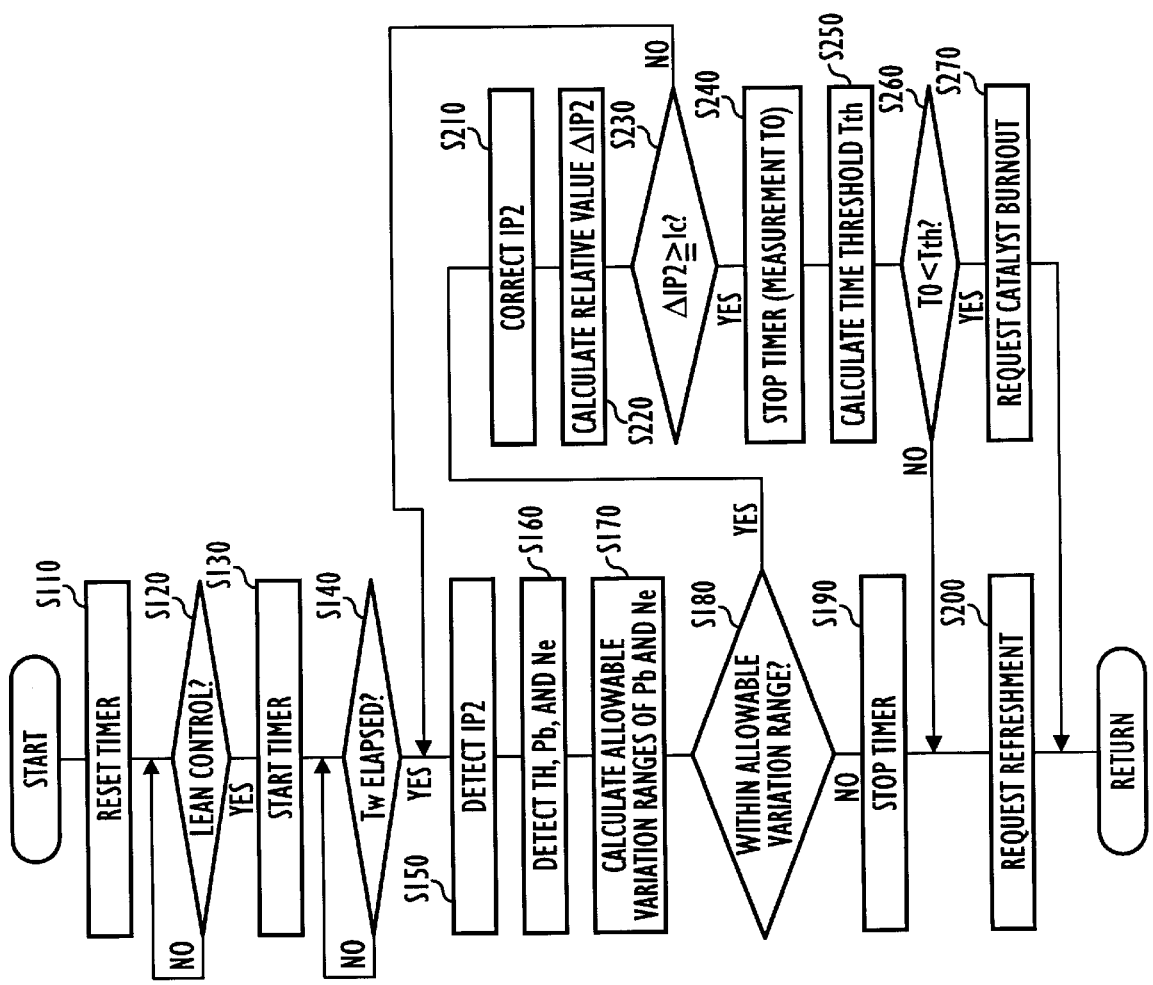
FIG. 5 is a flowchart showing a functional condition detection process which is repeatedly carried out in an ECU of the embodiment of FIG. 1.

As shown in FIG. 5, first, in S110 (S represents "step"), a timer for use in the process is reset. Subsequently, in S120, based on operation control information received from the engine control unit 52, the ECU 50 determines whether the engine control unit 52 has started lean control. Upon detecting the start of lean control, the ECU 50 proceeds to S130.

In S130, the ECU 50 starts the time which was reset in S110. Subsequently, in S140, the ECU 50 determines whether a waiting time Tw has elapsed.

During a certain time immediately after switching from normal control to lean control, the concentration of oxygen in the exhaust gas is unstable. Accordingly, the offset of the second pumping current IP2 varies, thereby disabling accurate detection. Thus, the waiting time Tw is set to a length such that variation in the second pumping current IP2 induced by switching the control mode is sufficiently settled.

Upon detecting elapse of the waiting time Tw in S140, the ECU 50 proceeds to S150. In S150, the ECU 50 reads the detection signal VIP2 to thereby detect the second pumping current IP2, namely, the ECU 50 serves as the second pumping-current detection means.

Next, in S160, serving as the temperature detection means and the inflow gas conditions detection means, the ECU 50 detects the temperature TH of the NOx sensor 2, the negative pressure Pb in the suction pipe, and the engine speed Ne using the temperature sensor 46, the pressure sensor 47, and the rotational speed sensor 48, respectively. Subsequently, in S170, the ECU 50 calculates allowable variation ranges for the negative pressure Pb in the suction pipe and the engine speed Ne.

The allowable variation ranges are determined by the steps of: calculating respective average values of the negative pressure Pb in the suction pipe and the engine speed Ne detected repeatedly in S160; and determining a range composed of each of the calculated average values, serving as a center value of the range, and a predetermined tolerance (for example, ±10%), as a set value for each of the allowable variation ranges.

The allowable variation ranges serve as reference values for detecting abrupt variations of the flow rate of exhaust gas flowing into the NOx occlusion catalyst S3, the concentration of NOx in the exhaust gas, and the air-fuel ratio. Exhaust gas conditions are not directly detected, but are indirectly detected based on operating conditions of the internal combustion engine S1, such as the engine speed Ne and the negative pressure Pb in the suction pipe which are determinants of the exhaust gas conditions.

Specifically, in the present embodiment, the second pumping current IP2 detected in S150 is compensated for temperature based on the sensor temperature TH, which will be described later. In the case of a great variation in operating conditions, sufficiently high accuracy may not be obtained even through compensated for temperature. To prevent such a problem, allowable variation ranges are defined in which a sufficiently high accuracy can be obtained by temperature compensation.

In S180, the ECU 50 judges whether the negative pressure Pb in the suction pipe and the engine speed Ne detected in S160 fall within the respective allowable variation ranges set in S170. When even either Pb or Ne fails to fall within the corresponding allowable variation range, the ECU 50 proceeds to S190 and stops the timer. Subsequently, in S200, the ECU 50 outputs a request for refreshment of the NOx occlusion catalyst S3 to the engine control unit 52 and terminates the detection process.

In S180, when the ECU 50 judges that both the negative pressure Pb in the suction pipe and the engine speed Ne fall within the respective allowable variation ranges, the ECU 50 proceeds to S210. In S210, serving as the second correction means, the ECU 50 corrects the second pumping current IP2 detected in S150 based on the sensor temperature TH detected in S160.

Specifically, in the present embodiment, current applied to the heater-energizing circuit 44 is controlled such that the temperature detected by the temperature sensor 46 becomes constant. However, when exhaust temperature drops temporarily in association with an increase in intake air volume during acceleration of the internal combustion engine S1 or when exhaust temperature rises temporarily in association with a decrease in intake air volume during deceleration of the internal combustion engine S1, the NOx sensor 2 is affected by the temperature variation. As a result, both the first pumping current IP1 and the second pumping current IP2 vary. Particularly, the second pumping current IP2 takes a relatively long time (about 1 minute) until it is stabilized. This is because once the concentration of oxygen in the first measurement space 20 deviates from a target concentration due to the first pumping current IP1 being affected by variations in exhaust temperature, it takes time to restore the oxygen concentration to the target concentration. This variation in oxygen concentration causes a variation in offset of the second pumping current IP2.

Figure 6:
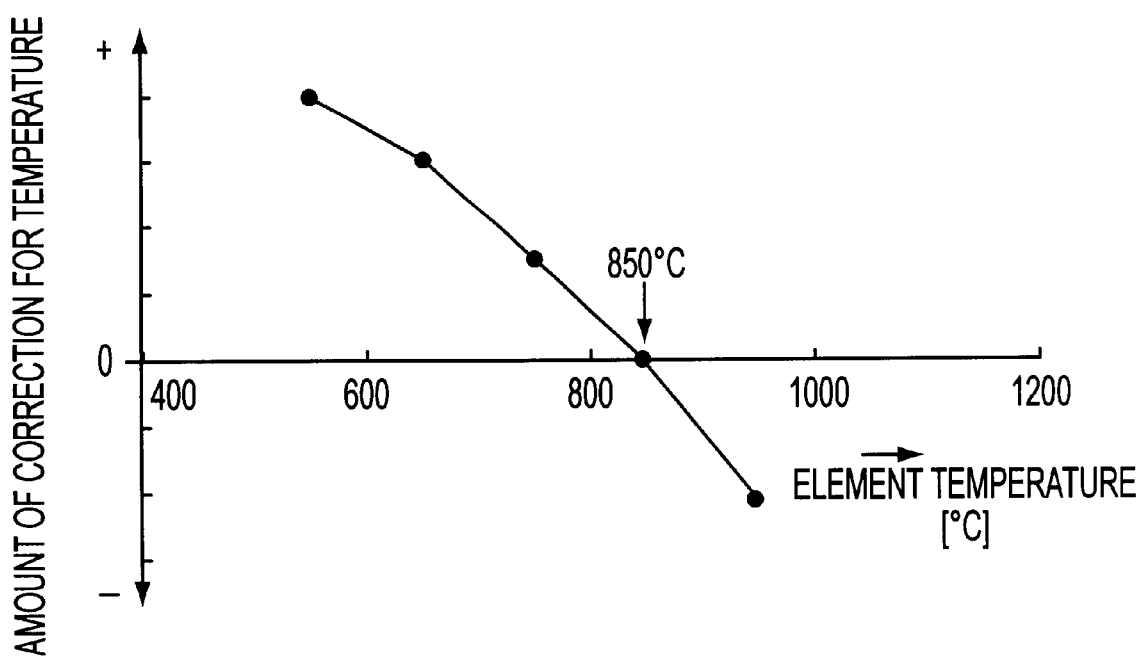
FIG. 6 is a graph showing an example of a map used for correcting the second pumping current for changes in temperature.

In the present embodiment, in order to accurately cancel variation in offset of the second pumping current IP2 regardless of abrupt variations in the exhaust temperature, the temperature of the NOx sensor 2 is measured by means of the temperature sensor 46, and the amount of temperature correction is determined based on the measured temperature and using, for example, the temperature correction map of FIG. 6. Based on the thus determined amount of temperature correction, the second pumping current IP2 is corrected.

In S220, using the corrected second pumping current IP2, the ECU 50 calculates a relative value ΔIP2 with respect to the second pumping current IP2o which is detected first (at time t1 in FIG. 4) after start of the timer (ΔIP2=IP2−IP2o). Subsequently, in S230, serving as the functional deterioration judgment means, the ECU 50 determines whether the relative value ΔIP2 is equal to or greater than a predetermined value Ic. In the case of a NO judgment, the ECU 50 considers that the NOx occlusion catalyst S3 still has occlusion capability (the catalyst S3 is not deteriorated yet), and returns to S150.

The predetermined value Ic is not particularly limited so long as the value Ic is smaller than the second pumping current IP2 as detected when the NOx occlusion catalyst becomes disabled and does not store NOx at all, but is preferably about 70% to 80% of the detected second pumping current IP2.

While the ECU 50 repeats the steps S150–S180 and S210–S230, NOx contained in the exhaust gas accumulates on the NOx occlusion catalyst S3 in the form of nitrate. As the amount of accumulated nitrate increases with the elapse of time, the NOx occlusion capability deteriorates, and the concentration of NOx in the measurement gas as measured at a location downstream of the NOx occlusion catalyst S3 increases. Accordingly, the second pumping current IP2 and its relative value ΔIP2 increase gradually.

As a result, the relative value ΔIP2 becomes equal to or greater than the predetermined value Ic, resulting in a YES judgment in S230. The ECU 50 then proceeds to S240. In S240, serving as the current-increasing-time measuring means, the ECU 50 stops the timer and records the reading of the timer as a measurement TO. Subsequently, in S250, serving as the allowable value setting means, the ECU 50 calculates a time threshold Tth used for detecting an anomaly in the occlusion capability of the NOx occlusion catalyst S3.

Specifically, the time threshold Tth is calculated in the following manner. The ECU 50 estimates the flow rate of exhaust gas and the concentration of NOx contained in the exhaust gas based on respective average values of the negative pressure Pb in the suction pipe and the engine speed Ne which are repeatedly detected in S160 while the timer is active. Based on the estimated flow rate and NOx concentration, the ECU 50 estimates the time required for the second pumping current IP2 to exceed the predetermined value Ic. The thus-estimated time is set as the time threshold Tth. Notably, the time threshold Tth may be determined using a map which contains as parameters an average negative pressure Pb in the suction pipe and an average engine speed Ne.

Subsequently, in S260, serving as the functional anomaly judgment means, the ECU 50 determines whether the measurement TO stored in S240 is smaller than the time threshold Tth. In the case of a NO judgment, the ECU 50 considers that the NOx occlusion catalyst S3 suffers functional deterioration due to accumulation of nitrate, and proceeds to S200. In S200, the ECU 50 outputs a request for refreshing of the NOx occlusion catalyst S3 to the engine control unit 52.

By contrast, in the case of a YES judgment in S260, the ECU 50 considers that the NOx occlusion catalyst S3 suffers an anomaly, such as accumulation of sulfate or exfoliation of an NOx storage material, and proceeds to S270. In S270, the ECU 50 outputs a request for catalyst burnout to the engine control unit 52 and then terminates the detection process.

Upon receipt of a request for refreshment from the ECU 50, the engine control unit 52 controls the operating conditions of the internal combustion engine S1 so as to temporarily establish a rich air-fuel ratio, thereby causing unburned gas to be emitted from the internal combustion engine S1. By reaction of the unburned gas with nitrate accumulated on the NOx occlusion catalyst S3, the NOx occlusion catalyst S3 is refreshed. Upon receiving a request for catalyst burnout from the ECU 50, the engine control unit 52 temporarily establishes such conditions so as to reduce sulfate accumulated on the NOx occlusion catalyst S3 by reaction, thereby refreshing (burning out) the NOx occlusion catalyst S3.

As described above, in the apparatus for detecting a functional condition of the NOx occlusion catalyst according to the present embodiment, when the relative value ΔIP2 with respect to the second pumping current IP2 detected at the time t1 after start of lean control, or operation control of the internal combustion engine S1 at a lean air-fuel ratio, increases by the predetermined value Ic, namely, when the amount of NOx leaking from the NOx occlusion catalyst S3 increases by a predetermined value, the occlusion capability of the NOx occlusion catalyst S3 is judged to have deteriorated. Also, when a time TO required for the relative value $\Delta IP2$ to increase by the predetermined value Ic is smaller than the time threshold Tth, the occlusion capability of the NOx occlusion catalyst S3 is judged to suffer an anomaly.

Thus, in the present embodiment, by using the relative value $\Delta IP2$, which cancels an offset of the second pumping current IP2, and by using variation of the second pumping current IP2 with respect to time (namely, slope), a functional deterioration of the NOx occlusion catalyst S3 is detected without using the absolute value of the second pumping current IP2. Thus, accurate detection can be carried out without being affected by an offset of the second pump current IP2.

Furthermore, in the present embodiment, based on the sensor temperature TH detected by the temperature sensor 46, an offset of the second pumping current IP2 is compensated for temperature variation. Thus, detection is not affected by variation of the sensor temperature, if any, during detection.

Also, in the present embodiment, parameters (the negative pressure Pb in the suction pipe and the engine speed Ne) indicative of operating conditions of the internal combustion engine S1 are successively detected. When either of the detected values falls outside the corresponding allowable variation ranges, this phenomenon is considered indicative of abrupt variation in operating conditions. Thus, judgment on functional deterioration is interrupted, and a request for refreshment is immediately output.

Accordingly, erroneous judgments are reliably prevented that would otherwise cause an unnecessary request for catalyst burnout and, which would impose a burden on the apparatus.

Second Embodiment

A second embodiment of the present invention is next described below.

The present embodiment is partially different from the first embodiment in the functional condition detection process performed by the ECU 50. Thus, only a different portion of the process will be described.

Figure 7:
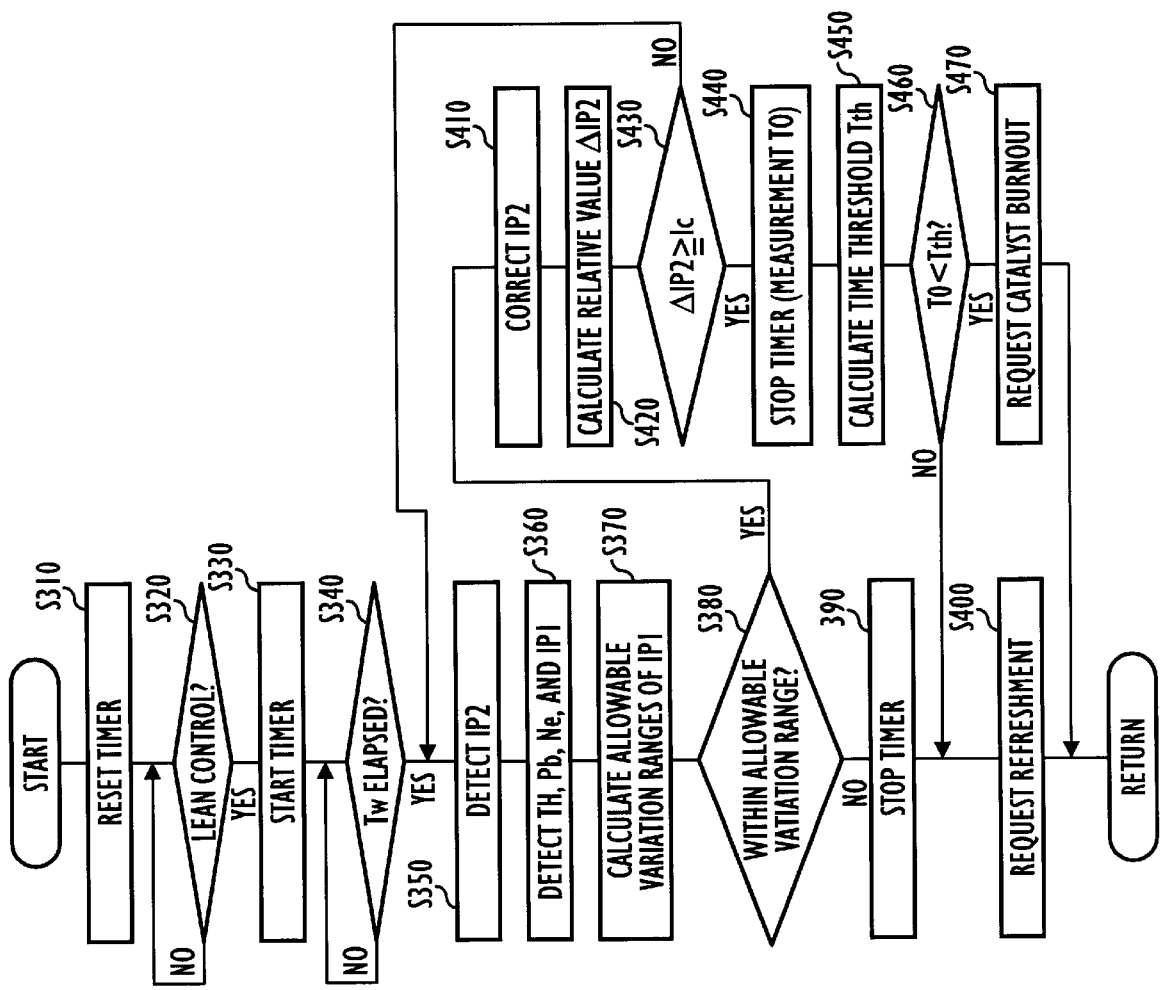
FIG. 7 is a flowchart showing a functional condition detection process in a second embodiment of the present invention.

FIG. 7 is a flowchart showing the functional condition detection process in the present embodiment. S310 to S350 are identical to the corresponding steps of the first embodiment. Specifically, the ECU 50 resets the timer (S310); when the operation control mode of the internal combustion engine S1 is switched to lean control (S320), the ECU 50 starts the timer (S330); and upon elapse of the waiting time Tw (S340), the ECU 50 starts to detect the second pumping current IP2 (S350).

In S360, the ECU 50 detects the sensor temperature TH, the negative pressure Pb in the suction pipe, and the engine speed Ne by means of the temperature sensor 46, the pressure sensor 47, and the rotational speed sensor 48, respectively. Also, serving as the oxygen concentration detection means, the ECU 50 detects the first pumping current IP1 by reading the detection signal VIP1.

Subsequently, in S370, the ECU 50 calculates an allowable variation range for the first pumping current IP1. The allowable variation range is determined by the steps of: calculating an average value of the first pumping current IP1 detected repeatedly in S360; and determining a range composed of each of the calculated average values, serving as a center value of the range, and a predetermined tolerance (for example, ±10%), as a set value for each of the allowable variation ranges.

In S380, the ECU 50 judges whether the first pumping current IP1 detected in S360 falls within its allowable variation range set in S370. In the case of a NO judgment, as in S190 and S200 of the first embodiment, the ECU 50 performs S390 and S400; specifically, the ECU 50 stops the timer, outputs a request for refreshing of the NOx occlusion catalyst S3 to the engine control apparatus 52, and then terminates the detection process.

In the case of a YES judgment in S380, the ECU 50 proceeds to S410. In S410, serving as the first and second correction means, the ECU 50 corrects the second pumping current IP2 detected in S350 based on the sensor temperature TH and the first pumping current IP1 detected in S360.

In the present embodiment, the ECU 50 directly detects variation of the oxygen concentration (airfuel ratio) of the measurement gas, in addition to temperature compensation performed in the first embodiment, to thereby more accurately correct the second pumping current IP2.

Figure 12:
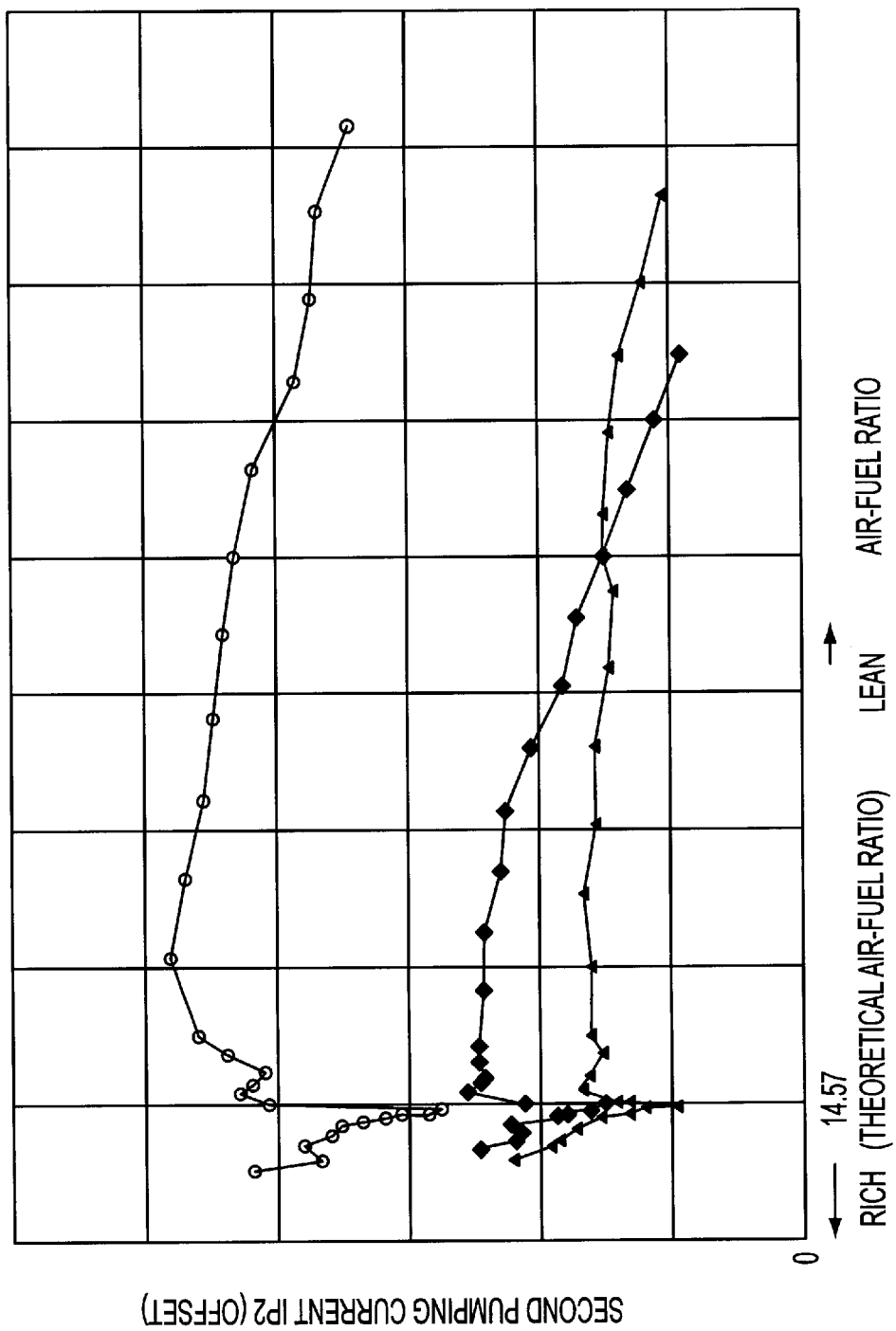
FIG. 12 is a graph showing the relationship between the second pumping current and the concentration of oxygen (air-fuel ratio) contained in a measurement gas which does not contain NOx.
Figure 13:
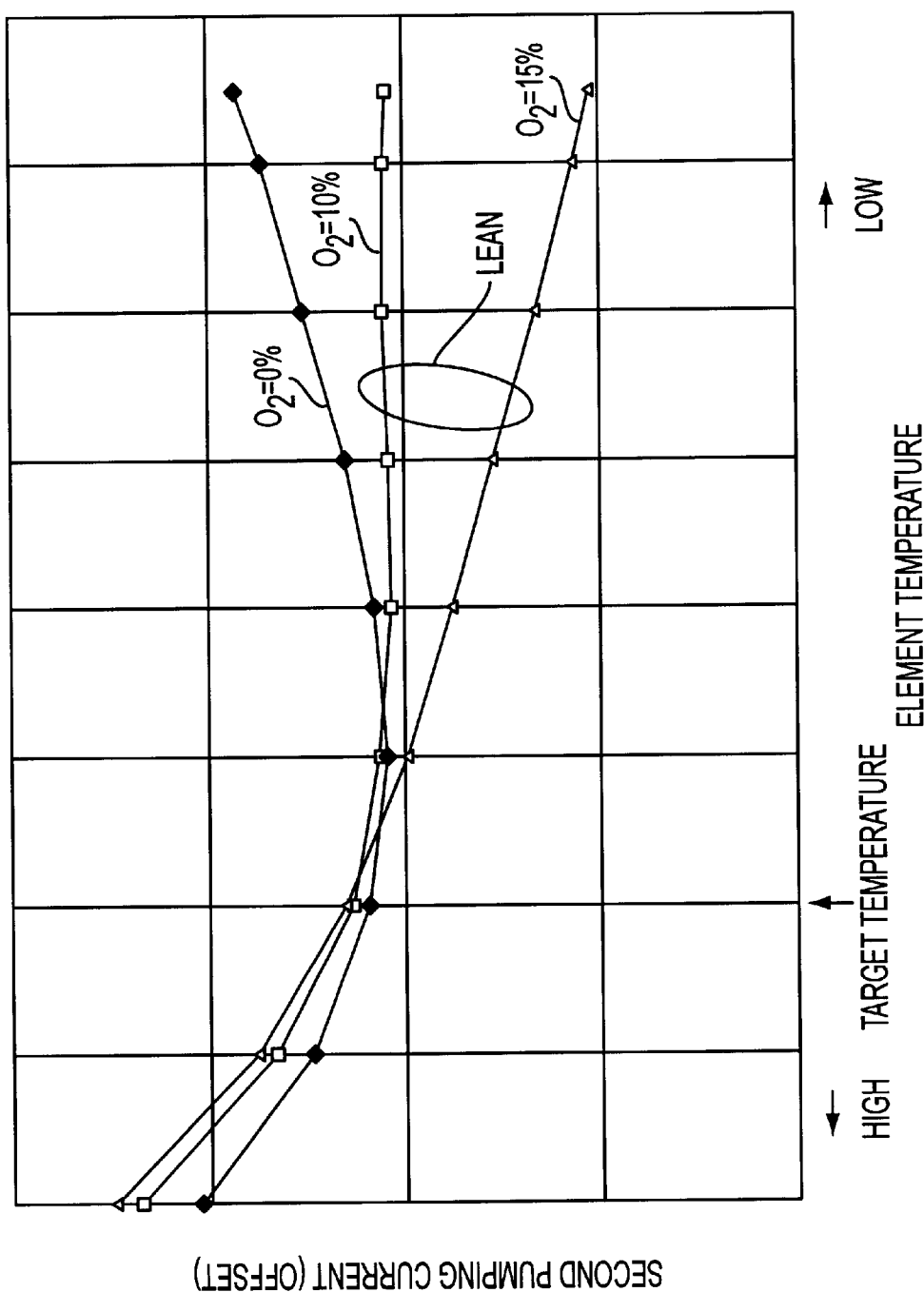
FIG. 13 is a graph showing a measured temperature characteristic of the second oxygen-pumping cell offset current.

Specifically, in order to make the second pumping current IP2 correspond only to the concentration of NOx contained in the measurement gas, offset values of the second pumping current IP2 corresponding to oxygen concentration values obtained by measuring a measurement gas not containing NOx (see FIG. 12) are stored in advance in the form of a map. Based on an offset value read from the map while the concentration of oxygen in the measurement gas as detected in the form of the first pumping current IP1 is used as a parameter, the ECU 50 corrects the detected second pumping current IP2.

Subsequently, in S420 to S470, as in S220 to S270 of the first embodiment, based on the corrected second pumping current IP2, the ECU 50 calculates the relative value $\Delta IP2$ with respect to the second pumping current IP2o which is detected first after start of the timer (S420). Subsequently, the ECU 50 judges whether the relative value $\Delta IP2$ is equal to or greater than the predetermined value Ic (S430). If the relative value $\Delta IP2$ is smaller than the predetermined value Ic, then the ECU 50 returns to S350. If the relative value $\Delta IP2$ is equal to or greater than the predetermined value Ic, then the ECU 50 stops the timer and records the reading of the timer as the measurement TO (S440). Subsequently, based on respective average values of the negative pressure Pb in the suction pipe and the engine speed Ne detected repeatedly in S360, the ECU 50 calculates the time threshold Tth (S450). Then, the ECU 50 judges whether the measurement TO stored in S440 is smaller than the time threshold Tth (S460). If the measurement TO is equal to or greater than the time threshold Tth, then the ECU 50 outputs a request for refreshment to the engine control unit 52. If the measurement TO is smaller than the time threshold Tth, then the ECU 50 outputs a request for catalyst burnout to the engine control unit 52 (S470) and then terminates the detection process.

As described above, according to the apparatus of the present embodiment for detecting a functional condition of the NOx occlusion catalyst, as in the case of the first embodiment, by using the relative value $\Delta IP2$ of the second pumping current IP2 and variation of the second pumping current IP2 with respect to time (namely, slope), a functional deterioration of the NOx occlusion catalyst S3 is detected without using the absolute value of the second pumping current IP2. Thus, accurate detection can be carried out without being affected by an offset of the second pumping current IP2.

Furthermore, in the present embodiment, based on not only the sensor temperature TH but also the first pumping current IP1, the second pumping current IP2 is corrected. Thus, accurate detection can be carried out without being affected by variation of the sensor temperature TH and variation of the concentration of oxygen (air-fuel ratio) in the measurement gas, if any, during detection.

Also, because the concentration of oxygen in the measurement gas is detected using the NOx sensor 2 with no need for employing a new sensor, environmental variation that affects the second pumping current IP2 can be detected more accurately. Accordingly, the second pumping current IP2 can be corrected accurately.

Figure 8A:
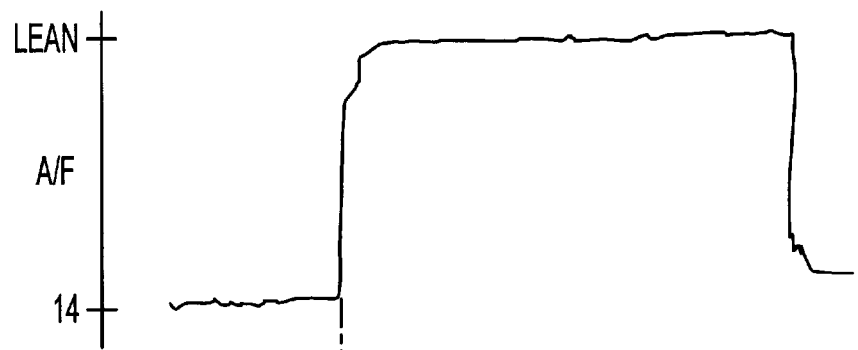
FIGS. 8(a) and (b) are waveform charts of the second pumping current detected when the NOx occlusion capability of the NOx occlusion catalyst is excessively deteriorated.
Figure 8B:
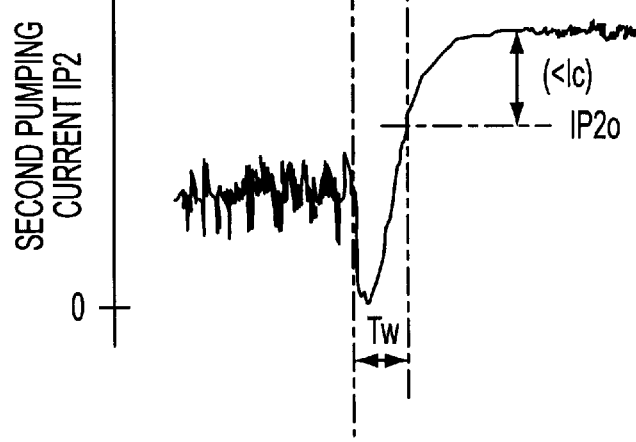

The present embodiment assumes that the first detected value IP2o, which serves as a reference value in calculating the relative value ΔIP2 of the second pumping current, is detected while the NOx occlusion catalyst S3 has sufficient NOx occlusion capability. When the occlusion capability of the NOx occlusion catalyst S3 is considerably deteriorated due to, for example, exfoliation of a large amount of an NOx storage material, the second pumping current IP2 increases abruptly immediately after the operation control mode is switched to lean control, as shown in FIGS. 8(a) and (b). In this case, at time t1 when detection is first carried out after elapse of the waiting time Tw, the second pumping current IP2 has already increased greatly. Thus, if the second pumping current IP2 detected at time t1 is used as a reference value in calculating the relative value ΔIP2 of the second pumping current, the relative value ΔIP2 will not exceed the predetermined value Ic. As a result, control may be disabled.

To prevent the above problem, for example, the upper limit of the timer value may be predetermined. A time-out may be considered as an indication of an anomaly in the occlusion capability of the NOx occlusion catalyst S3, and a request for catalyst burnout may be output.

Alternatively, a plurality of predetermined values may be set stepwise for comparison with the second pumping current IP2. The slope of the second pumping current IP2 is obtained for each span between the adjacent predetermined values. Based on the thus-obtained slopes, a determination can be made as to whether the above-mentioned anomaly is present.

Third Embodiment

A third embodiment of the present invention is next described below.

The present embodiment is different from the first and second embodiments in the functional condition detection process performed by the ECU 50. Thus, only a different portion of the process will be Thus, only a different portion of the process will be described.

In the present embodiment, a request for refreshment is periodically output at constant intervals of time, and the functional condition detection process is only adapted to output a request for catalyst burnout.

Figure 9:
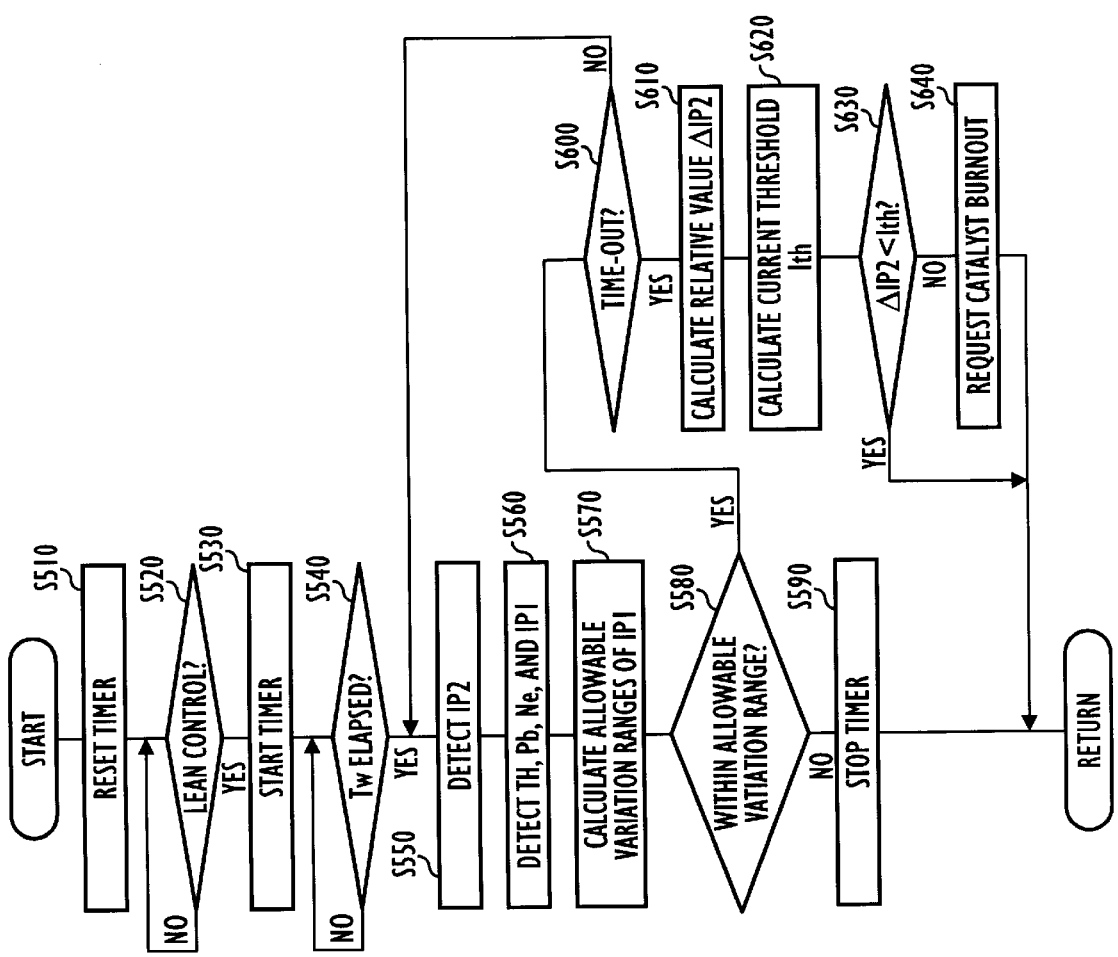
FIG. 9 is a flowchart showing a functional condition detection process in a third embodiment of the present invention.

FIG. 9 is a flowchart showing the functional condition detection process in the present embodiment. S510 to S590 are identical to S310 to S390 of the second embodiment. Specifically, the ECU 50 resets the timer (S510); when the operation control mode of the internal combustion engine S1 is switched to lean control (S520), the ECU 50 starts the timer (S530); and upon elapse of the waiting time Tw (S540), the ECU 50 starts to detect the second pumping current IP2 (S550). In this detection process, being different from the timers used in the first and second embodiments, the timer to be started in S530 goes into time-out upon measuring a predetermined time Tc.

The ECU 50 detects the sensor temperature TH, the negative pressure Pb in the suction pipe, and the engine speed Ne, and reads the detection signal VIP1 (S560). Then, the ECU 50 calculates an allowable variation range for the first pumping current IP1 (S570). If the first pumping current IP1 detected in S550 falls outside the allowable variation range set in S570 (a NO judgment in S580), then the ECU 50 stops the timer (S590) and then terminates the detection process.

If the first pumping current IP1 detected in S560 falls within the allowable variation range set in S570 (a YES judgment in S580), then the ECU 50 proceeds to S600.

In S600, the ECU 50 determines whether the timer has finished measuring the predetermined time Tc (time-out). If a time-out is not effected, then the ECU 50 returns to S550. If a time-out is effected, then the ECU 50 proceeds to S610.

In S610, serving as the current-increase measuring means, the ECU 50 calculates the relative value ΔIP2 between the second pumping current IP2o as detected first after start of the timer and the second pumping current IP2e as detected last immediately before the timer goes into time-out (ΔIP2= IP2o−IP2e), namely, an increase in the second pumping current IP2 as measured during a fixed time interval (Tc−Tw). Subsequently, in S620, serving as the allowable value setting means, the ECU 50 calculates a current threshold Ith used for detecting an anomaly in the occlusion capability of the NOx occlusion catalyst S3.

Notably, the current threshold Ith is calculated in the following manner. The ECU 50 estimates the flow rate of exhaust gas and the concentration of NOx in the exhaust gas based on respective average values of the negative pressure Pb in the suction pipe and the engine speed Ne which are repeatedly detected in S560 while the timer is active. Based on the estimated flow rate and NOx concentration, the ECU 50 estimates an increase in the second pumping current IP2 during the fixed time (Tc−Tw). Based on the thus-estimated increase, the current threshold Ith is set.

The second pumping currents IP2o and IP2e used in calculating the relative value ΔIP2 may be corrected based on the sensor temperature TH and the first pumping current IP1 detected in S560 in a manner similar to that in S210 and S410 of the first and second embodiments, respectively.

Figure 10A:
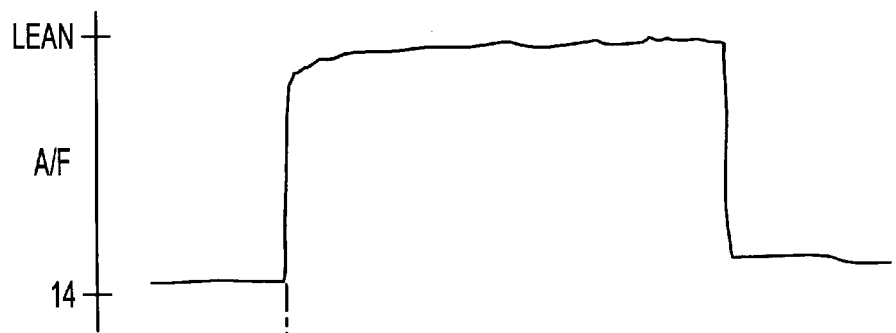
FIGS. 10(a)–(c) are graphs explaining a functional anomaly detection method in accordance with a third embodiment of the present invention.
Figure 10B:
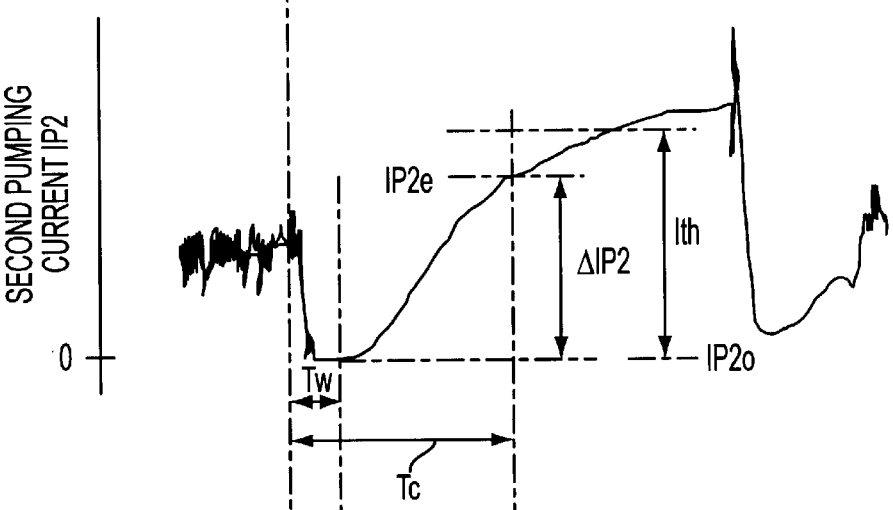
Figure 10C:
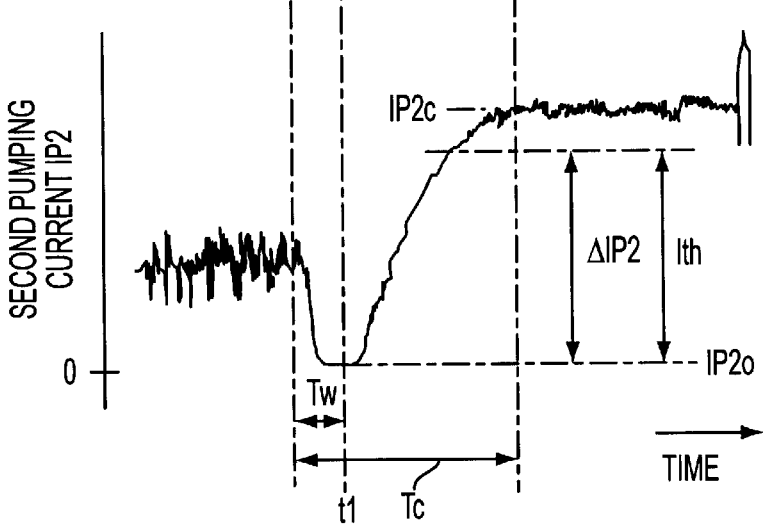
Figure 11A:
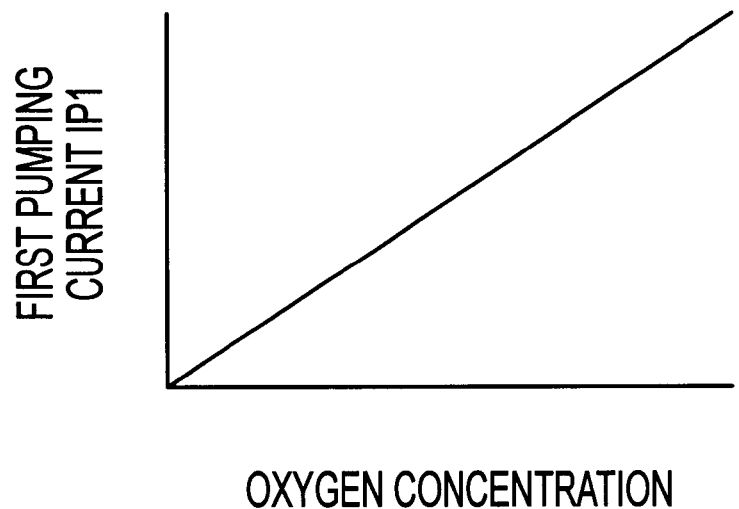
FIGS. 11(a) and (b) are graphs schematically showing the relationship between oxygen concentration and the first pumping current, as well as the relationship between NOx concentration and the second pumping current.
Figure 11B:
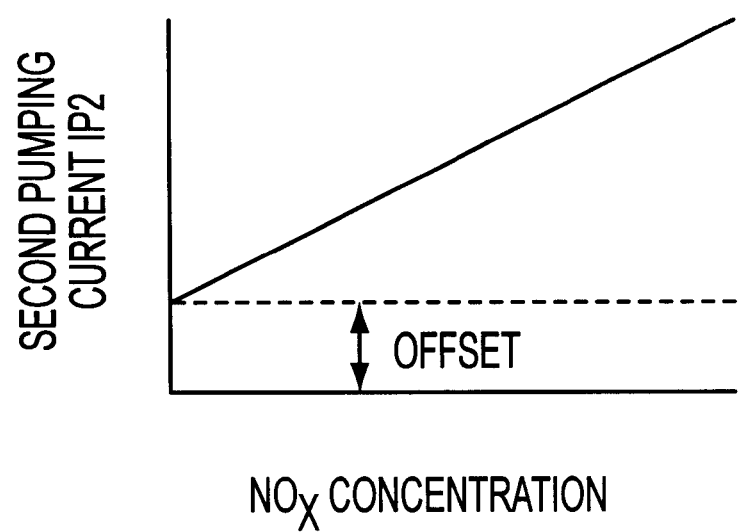

In S630, the ECU 50 judges whether the relative value ΔIP2 calculated in S610 is smaller than the current threshold Ith calculated in S620. When, for example, as shown in FIG. 10(b), the relative value ΔIP2 of the second pumping current is smaller than the current threshold Ith (namely, the slope of the second pumping current IP2 is smaller than the corresponding allowable value), and thus the a YES judgment is performed in S630, the ECU 50 terminates the detection process. By contrast, when, for example, as shown in FIG. 10(c), the relative value ΔIP2 of the second pumping current is equal to or greater than the current threshold Ith (namely, the slope of the second pumping current IP2 is equal to or greater than the corresponding allowable value), and thus a NO judgment is performed in S630, the ECU 50 proceeds to S640. In S640, the ECU 50 outputs a request for catalyst burnout to the engine control unit 52. The ECU 50 then terminates the present process.

As in the case of FIG. 4, FIGS. 10(a)–(c) show graphs of the measured second pumping current IP2 of the NOx sensor 2, which is located downstream of the NOx occlusion catalyst S3, when the engine control unit 52 switches the operation control mode of the internal combustion engine S1 from operation control at a theoretical air-fuel ratio (hereinafter referred to as normal control) to operation control at a lean air-fuel ratio (hereinafter referred to as lean control).

As described above, the slope of the second pumping current IP2 after start of operation control at a lean air-fuel ratio is obtained based on the time TO required for the second pumping current IP2 to increase by a predetermined value, as in the case of the first and second embodiments. Alternatively, the slope of the second pumping current IP2 may be obtained based on an increase in ΔIP2 of the second pumping current as measured during the fixed time (Tc–Tw). This also enables the present embodiment to produce an effect similar to that produced by the first and second embodiments.

Notably, in the present embodiment, the ECU 50 judges whether the occlusion capability of the NOx occlusion catalyst suffers an anomaly, based on the increase in ΔIP2 of the second pumping current as measured during the fixed time (Tc–Tw). Alternatively, this judgment may be performed based on an integral value of the second pumping current over the fixed time (Tc–Tw). In this case, even when the second pumping current IP2 suffers noise, an adverse effect of the noise can be lessened; thus, judgment can be performed highly reliably.

The present invention is not limited to the above-described embodiments, but may be embodied in various other forms.

For example, in the above-described embodiments, in S120, S320 and S520, the ECU 50 judges whether the operation control mode of the internal combustion engine S1 is switched to lean control, based on operation control information received from the engine control unit 52. However, the judgment may be performed by determining whether the first pumping current IP1, which is proportional to the concentration of oxygen in the measurement gas, assumes a value corresponding to an oxygen concentration associated with a lean air-fuel ratio.

In th is case, in contrast to the case of utilizing operation control information received from the engine control unit 52, an actual variation of the exhaust gas condition is detected. Thus, a functional condition of the NOx occlusion catalyst can be handled in quick response to the variation of an exhaust gas condition.

In the above-described embodiments, the temperature TH of the NOx sensor 2 is obtained using the temperature sensor 46. However, as described in Japanese Patent Application No. 8-296676 filed by the applicants of the present invention, the resistance of the Vs cell 6 may be detected, and the temperature of the NOx sensor 2 may be obtained based on the detected resistance.

Furthermore, in the above-described embodiments, a time threshold is set based on the negative pressure Pb in the suction pipe and the engine speed Ne. However, any parameter may be used so long as it has an effect on the flow rate of exhaust gas and the concentration of NOx in the exhaust gas.

Also, in the above-described second embodiment, the oxygen concentration is detected using the NOx sensor 2. However, a separate oxygen sensor may be employed for detecting the oxygen concentration.

Fourth Embodiment

The process of detecting a functional condition of the NOx occlusion catalyst S3 by the ECU 50 in accordance with a fourth embodiment of the present invention will next be described following the flowchart of FIG. 15.

Concurrent with execution of the detection process, a process is executed for reading the sensor temperature TH from the temperature sensor 46 and controlling the sensor temperature to a constant activation temperature. This process is repeatedly executed after the NOx sensor 2 is activated by applying current to the heaters 12 and 14.

Figure 15:
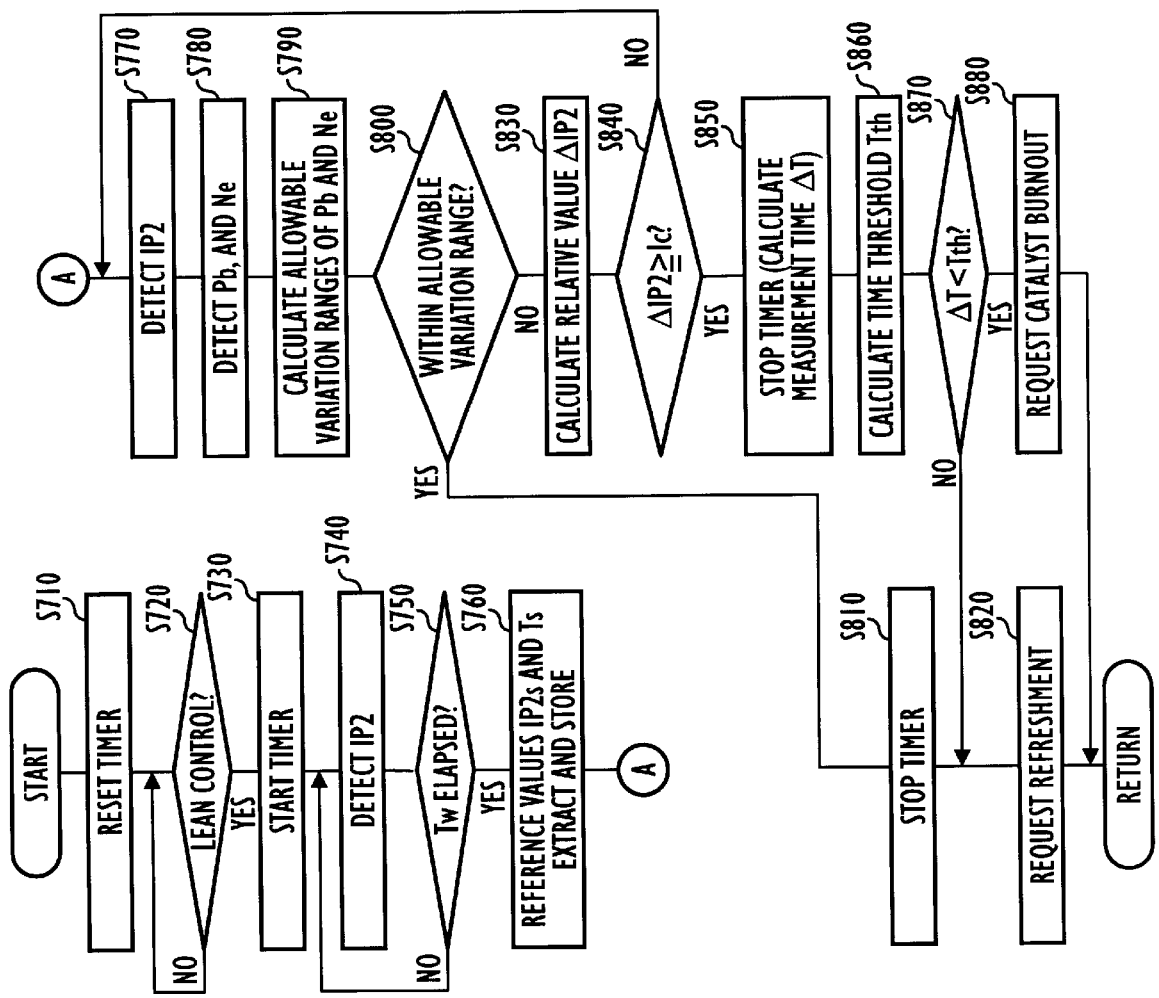
FIG. 15 is a flowchart showing a functional condition detection process which is repeatedly carried out in an ECU in accordance with a fourth embodiment of the present invention.
Figure 16A:
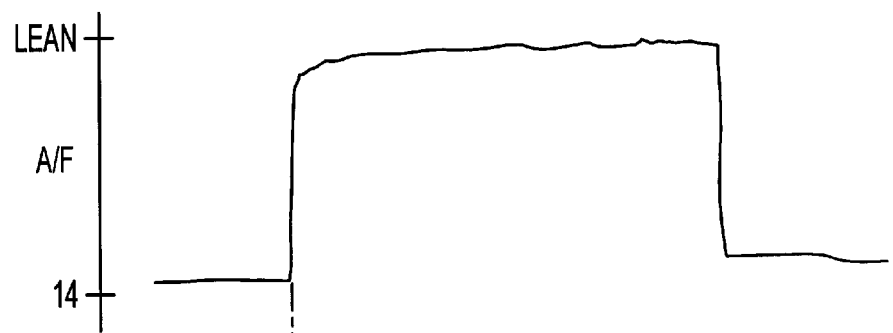
FIGS. 16(a)–(c) are waveform charts for explaining problems involved in detecting a functional condition of an NOx occlusion catalyst in accordance with the embodiment of FIG. 15.
Figure 16B:
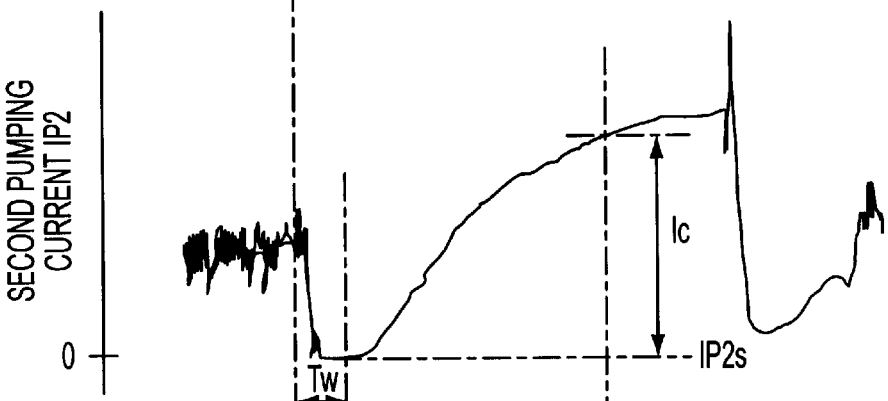
Figure 16C:
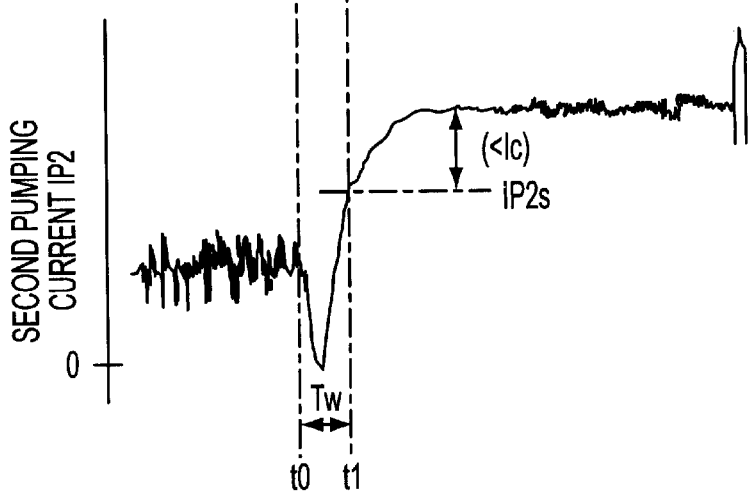

As shown in FIG. 15, first, in S710 (S represents "step"), a timer to be used in the process is reset. Subsequently, in S720, the ECU 50 judges whether the engine control unit 52 is performing lean control. Upon detection of lean control being in effect, the ECU 50 proceeds to S730.

The ECU 50 may judge whether lean control is in effect, on the basis of operation control information received from the engine control unit 52. Alternatively, the ECU 50 may detect the first pumping current IP1 by reading the detection signal VIP1 and may judge whether the detected first pumping current IP1 is indicative of an oxygen concentration corresponding to a lean air-fuel ratio, thereby judging whether lean control is in effect.

In S730, the ECU 50 starts the time which was reset in S710. Subsequently, in S740, the ECU 50 reads the detection signal VIP2 to thereby detect the second pumping current IP2, and stores the detected value together with the associated timer value. In S750, the ECU 50 judges whether the waiting time Tw has elapsed. In the case of a NO judgment, the ECU 50 performs S740 again.

Notably, while a NO judgment is in effect in S750, the ECU 50, in S740, repeatedly detects the second pumping current IP2 at intervals of about 5 to 20 ms (sampling rate: 50 Hz to 200 Hz). The waiting time Tw is set to a length during which variation in the second pumping current IP2 induced by switching the control mode from normal control to lean control sufficiently settles.

When the elapse of the waiting time Tw after start of the timer causes a YES judgment in S750, the ECU 50 proceeds to S760. In S760, the ECU 50 extracts a minimum value, together with an associated timer value, from among values of the second pumping current IP2 which have been stored through repeated detection in S740 during the waiting time Tw, and stores the extracted minimum value and timer value as a reference second pumping current IP2s and a reference timer value Ts, respectively, (see FIGS. 14(*b*) and 14(*c*)). When a plurality of minimum values of the second pumping current IP2 are present, the last detected minimum value is extracted as the reference second pumping current IP2s.

Herein, a minimum value of the second pumping current IP2 is extracted after elapse of the waiting time Tw. However, the extraction of the minimum value of the second pumping current IP2 may be performed such that during the waiting time Tw, upon each detection of the second pumping current IP2, the detected value is compared with stored values in order to extract the minimum value.

In subsequent S770, as in S740, the ECU 50 reads the detection signal VIP2 to thereby detect the second pumping current IP2. The S770 step is repeatedly performed, which will be described later. Specifically, in S770, the ECU 50 repeatedly detects the second pumping current IP2 at a detection period longer lower than that in S740, i.e., at intervals of about 20 to 100 ms (sampling rate: 1 Hz to 50 Hz).

In S780, the ECU 50 detects the negative pressure Pb in the suction pipe and the engine speed Ne using of the pressure sensor 47 and the rotational speed sensor 48, respectively. Subsequently, in S790, the ECU 50 calculates allowable variation ranges for the negative pressure Pb in the suction pipe and the engine speed Ne.

The allowable variation ranges are determined by the steps of: calculating respective average values of the negative pressure Pb in the suction pipe and the engine speed Ne which are repeatedly detected in S780 after the timer is started in S730; and determining a range composed of each of the calculated average values, serving as a center value of the range, and a predetermined tolerance (for example, ±10%), as a set value for each of the allowable variation ranges.

The allowable variation ranges serve as reference values for detecting abrupt variations of the flow rate of exhaust gas flowing into the NOx occlusion catalyst S3, the concentration of NOx in the exhaust gas, and air-fuel ratio. Exhaust gas conditions are not directly detected, but are indirectly detected based on operating conditions of the internal combustion engine S1, such as the engine speed Ne and the negative pressure Pb in the suction pipe which are determinants of exhaust gas conditions.

Specifically, when the concentrations of oxygen and NOx in the exhaust gas vary greatly due to, for example, variation in operating conditions, the second pumping current IP2 may not be detected at a sufficiently high accuracy. Thus, in the present embodiment, the allowable variation ranges are set so as to reliably obtain a sufficiently high accuracy, thereby preventing an erroneous operation.

In S800, the ECU 50 judges whether the negative pressure Pb in the suction pipe and the engine speed Ne detected in S780 fall within the respective allowable variation ranges set in S790. When even either Pb or Ne fails to fall within the corresponding allowable variation range, the ECU 50 proceeds to S810 and stops the timer. Subsequently, in S820, the ECU 50 outputs a request for refreshment of the NOx occlusion catalyst S3 to the engine control unit 52 and terminates the detection process.

In S800, when the ECU 50 judges that both the negative pressure Pb in the suction pipe and the engine speed Ne fall within the respective allowable variation ranges, the ECU 50 proceeds to S830. In S830, the ECU 50 calculates a relative value $\Delta IP2$ of a latest second pumping current IP2e detected in S770 with respect to the reference second pumping current IP2s stored in S760 ($\Delta IP2 = IP2e - IP2s$).

In S840, the ECU 50 judges whether the relative value $\Delta IP2$ calculated in S830 is equal to or greater than a predetermined value Ic. In the case of a NO judgment, the ECU 50 considers that the NOx occlusion catalyst S3 still has the occlusion capability (the catalyst S3 is not deteriorated yet), and returns to S770.

The predetermined value Ic is not particularly limited so long as the value Ic is smaller than the second pumping current IP2 as detected when the NOx occlusion catalyst becomes disabled and does not store NOx at all, but is preferably about 70% to 80% of the detected second pumping current IP2.

While the ECU 50 repeats the steps S770–S800, S830 and S840, the NOx occlusion capability deteriorates, and the concentration of NOx in the measurement gas as measured at a location downstream of the NOx occlusion catalyst S3 increases. Accordingly, the second pumping current IP2 and its relative value $\Delta IP2$ increase gradually.

As a result, the relative value $\Delta IP2$ becomes equal to or greater than the predetermined value Ic, resulting in a YES judgment in S840. The ECU 50 proceeds to S850. In S850, the ECU 50 stops the timer and calculates a measurement time $\Delta T$ based on the reading Te of the stopped timer and the reference timer value Ts ($\Delta T = Te - Ts$). Subsequently, in S860, the ECU 50 calculates a time threshold Tth used for detecting an anomaly in the occlusion capability of the NOx occlusion catalyst S3.

Specifically, the time threshold Tth is calculated in the following manner. The ECU 50 estimates the flow rate of exhaust gas and the concentration of NOx in the exhaust gas based on respective average values of the negative pressure Pb in the suction pipe and the engine speed Ne which are repeatedly detected in S780 while the timer is active. Based on the estimated flow rate and NOx concentration, the ECU 50 estimates the time required for the second pumping current IP2 to exceed the predetermined value Ic. The thus-estimated time is set as the time threshold Tth. Notably, the time threshold Tth may be determined using a map which contains as parameters an average negative pressure Pb in the suction pipe and an average engine speed Ne.

Subsequently, in S870, the ECU 50 judges whether the measurement time $\Delta T$ calculated in S850 is smaller than the time threshold Tth set in S860. In the case of a NO a judgment, the ECU 50 considers that the NOx occlusion catalyst S3 suffers functional deterioration due to accumulation of nitrate, and proceeds to S820. In S820, the ECU 50 outputs a request for refreshing of the NOx occlusion catalyst S3 to the engine control unit 52.

By contrast, in the case of a YES judgment in S870, the ECU 50 considers that the NOx occlusion catalyst S3 suffers an anomaly, such as accumulation of sulfate or exfoliation of an NOx storage material, and proceeds to S880. In S880, the ECU 50 outputs a request for catalyst burnout to the engine control unit 52 and then terminates the detection process.

Upon receiving a request for refreshment from the ECU 50, the engine control unit 52 controls operating conditions of the internal combustion engine S1 so as to temporarily establish a rich air-fuel ratio, thereby causing unburned gas to be emitted from the internal combustion engine S1. By reaction of the unburned gas with nitrate accumulated on the NOx occlusion catalyst S3, the NOx occlusion catalyst S3 is refreshed. Upon receiving a request for catalyst burnout from the ECU 50, the engine control unit 52 temporarily establishes such conditions as to reduce sulfate accumulated on the NOx occlusion catalyst S3 by reaction, thereby refreshing (burning out) the NOx occlusion catalyst S3.

In the detection process described above, the steps S720 to S760 correspond to the minimum value detection means of the present invention, and the steps S830 to S870 correspond to the functional condition judgment means of the present embodiment.

As described above, the apparatus of the present embodiment for detecting a functional condition of the NOx occlusion catalyst does not use an absolute value of the second pumping current IP2, but uses the relative value $\Delta IP2$ of the second pumping current, which cancels an offset of the second pumping current IP2, in judging a functional condition of the NOx occlusion catalyst S3 (whether the NOx occlusion catalyst S3 suffers a functional deterioration or a functional anomaly). Thus, accurate judgment can be performed.

Furthermore, in the present embodiment, a minimum value of the second pumping current IP2s as detected during the waiting time Tw after start of lean control is used as the reference second pumping current IP2s, which serves as a reference value in calculating the relative value $\Delta IP2$ of the second pumping current. Thus, even when, due to excessive deterioration in the occlusion capability of the NOx occlusion catalyst, the second pumping current IP2 has already increased greatly at the time of elapse of the waiting time Tw, a functional condition of the NOx occlusion catalyst can be reliably judged.

Thus, by using the detection apparatus of the present embodiment, improved reliability of an exhaust gas purification system using the NOx occlusion catalyst can be obtained.

Also, in the present embodiment, parameters (the negative pressure Pb in the suction pipe and the engine speed Ne) indicative of operating conditions of the internal combustion engine S1 are successively detected. When either of the detected values falls outside the corresponding allowable variation range, this phenomenon is considered indicative of abrupt variation of operating conditions. Thus, judgment on functional deterioration is interrupted, and a request for refreshment is immediately output.

Accordingly, an erroneous judgment can be reliably prevented that would otherwise cause an unnecessary request for catalyst burnout and which would impose a burden on the apparatus. Thus, the reliability and durability of the apparatus can be enhanced.

The present invention is not limited as described above, but may be embodied in various forms.

For example, in the above-described embodiment, the detection of the second pumping current IP2 is performed at high speed only during the waiting time Tw. However, the detection of the second pumping current IP2 may be performed at high speed after the elapse of the waiting time Tw if the processing capability allows it.

Also, in the above-described embodiment, a detected value of the second pumping current IP2 is used as such for calculating the relative value ΔIP2. However, the second pumping current IP2 may be corrected based on the sensor temperature TH detected by the temperature sensor 46 and the first pumping current IP1 indicative of the concentration of oxygen in the measurement gas, and the thus-corrected second pumping current IP2 may be used for calculating the relative value ΔIP2. In this case, even when, during execution of control, the offset of the second pumping current IP2 varies according to variation in the sensor temperature TH and the concentration of oxygen (air-fuel ratio) in the measurement gas, such an offset variation is compensated for, thereby enabling more accurate detection.

Furthermore, in the above-described embodiment, a minimum value of the second pumping current IP2 as detected during the waiting time Tw is used as the reference second pumping current IP2s. However, if, for some reason, there is a certain danger that the reference second pumping current IP2s will be set to a large value, and consequently the relative value ΔIP2 of the second pumping current will be unable to exceed the predetermined value Ic even when the NOx occlusion catalyst is completely disabled from occluding NOx, an upper limit may be predetermined for a timer value. The case of time-out may be considered as an indication of an anomaly in the occlusion capability of the NOx occlusion catalyst S3, and a request for catalyst burnout may be output.

Furthermore, in the above-described embodiment, a time threshold is set based on the negative pressure Pb in the suction pipe and the engine speed Ne. However, any parameter may be used so long as it has an effect on the flow rate of exhaust gas and the concentration of NOx in the exhaust gas.

While the invention has been described in detail and with reference to specific embodiments therefore, it will be apparent to one skilled in the art that various changes and modifications can be made therein without departing from the spirit and scope thereof.

What is claimed is:

1. An apparatus for detecting a functional condition of an NOx occlusion catalyst, comprising an NOx sensor disposed in an exhaust pipe of an internal combustion engine at a location downstream of the NOx occlusion catalyst, said NOx sensor including a first measurement space having a first oxygen-pumping cell and an oxygen-concentration-measuring cell and communicating with a measurement gas via a first diffusion-controlling layer; a second measurement space having a second oxygen-pumping cell and communicating with the first measurement space via a second diffusion-controlling layer; and a heater for heating said cells to a predetermined active temperature, said apparatus further comprising:
first pumping-current control means for controlling the concentration of oxygen in said first measurement space to a constant level by applying a first pumping current to said first oxygen-pumping cell such that an output voltage from said oxygen-concentration-measuring cell is maintained at a constant value;
constant-voltage application means for applying a constant voltage to said second oxygen-pumping cell in a direction such that oxygen is pumped out from said second measurement space;
second pumping-current detection means for detecting a second pumping current which flows through said second oxygen-pumping cell according to the concentration of NOx in the measurement gas;
minimum value detection means for detecting during operation control of the internal combustion engine at a lean air-fuel ratio a minimum value of the second pumping current during a predetermined waiting time after start of operation control of the internal combustion engine at a lean air-fuel ratio; and
functional condition judgment means for judging a functional condition of said NOx occlusion catalyst based on a relative value calculated as the difference between a value of the second pumping current detected by said second pumping-current detection means after elapse of the waiting time and the minimum value of the second pumping current detected by said minimum value detection means.

2. The apparatus for detecting a functional condition of an NOx occlusion catalyst as claimed in claim 1, wherein said minimum value detection means comprises means for detecting the start of operation control of the internal combustion engine at a lean air-fuel ratio based on variation in the first pumping current.

3. The apparatus for detecting a functional condition of an NOx occlusion catalyst as claimed in claim 1 or 2, wherein said functional condition judgment means comprises means for judging that the occlusion capability of said NOx occlusion catalyst has deteriorated when the relative value of the second pumping current exceeds a predetermined value.

4. The apparatus for detecting a functional condition of an NOx occlusion catalyst as claimed in claim 1 or 2, wherein said functional condition judgment means comprises means for judging that an anomaly has occurred in the occlusion capability of said NOx occlusion catalyst when a time-course variation rate of the relative value of the second pumping current becomes greater than a predetermined allowable value.

5. An apparatus for detecting a functional condition of an NOx occlusion catalyst, comprising an NOx sensor for detecting NOx concentration disposed in an exhaust pipe of an internal combustion engine at a location downstream of said NOx occlusion catalyst, said internal combustion engine being subjected to operation control at a lean air-fuel ratio and emitting an exhaust gas containing NOx, said apparatus further comprising:

(a) minimal value detection means for detecting during operation control of the internal combustion engine at a lean-air fuel ratio a minimum value of the NOx concentration of the exhaust gas downstream of said NOx occlusion catalyst during a predetermined waiting time after start of operation control of the internal combustion engine at a lean air-fuel ratio;

(b) means for calculating the difference between the NOx concentration detected after elapse of the waiting time and the minimum value of the NOx concentration as a relative value; and (c) functional condition judgment means for judging a functional condition of the NOx occlusion catalyst based on said relative value.

6. The apparatus for detecting a functional condition of an NOx occlusion catalyst as claimed in claim 5, which comprises means for judging that the occlusion capability of said NOx occlusion catalyst has deteriorated when said relative value exceeds a predetermined value.

7. The apparatus for detecting a functional condition of an NOx occlusion catalyst as claimed in claim 5, which comprises means for judging that an anomaly has occurred in the occlusion capability of said NOx occlusion catalyst when a time-course variation rate of said relative value exceeds a predetermined allowable value.

8. A method for detecting a functional condition of an NOx occlusion catalyst, wherein an NOx sensor is disposed in an exhaust pipe of an internal combustion engine at a location downstream of said NOx occlusion catalyst, said internal combustion engine being subjected to operation control at a lean air-fuel ratio and emitting an exhaust gas containing NOx, said method comprising the steps of:

(a) detecting during operation control of the internal combustion at a lean air-fuel ratio the NOx concentration of said exhaust gas downstream of said NOx occlusion catalyst, including detecting a minimum value of the NOx concentration of exhaust gas downstream of said NOx occlusion catalyst during a predetermined waiting time after start of operation control of the internal combustion engine at a lean air-fuel ratio;

(b) calculating the difference between the NOx concentration detected after elapse of the waiting time and the minimum value of the NOx concentration as a relative value; and (c) judging a functional condition of the NOx occlusion catalyst based on said relative value.

9. The method for detecting a functional condition of an NOx occlusion catalyst as claimed in claim 8, which comprises judging that the occlusion capability of said NOx occlusion catalyst has deteriorated when said relative value exceeds a predetermined value.

10. The method for detecting a functional condition of an NOx occlusion catalyst as claimed in claim 8, which comprises judging that an anomaly has occurred in the occlusion capability of said NOx occlusion catalyst when a time-course variation rate of said relative value exceeds a predetermined allowable value.

\* \* \* \* \*